(12) United States Patent
Kumada et al.

(10) Patent No.: US 9,481,713 B2
(45) Date of Patent: *Nov. 1, 2016

(54) SELF-ASSEMBLING PEPTIDES INCORPORATING MODIFICATIONS AND METHODS OF USE THEREOF

(71) Applicant: Massachusetts Institute of Technology, Cambridge, MA (US)

(72) Inventors: Yoshiyuki Kumada, Brookline, MA (US); Shuguang Zhang, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,147

(22) Filed: Apr. 28, 2014

(65) Prior Publication Data

US 2014/0322279 A1    Oct. 30, 2014

Related U.S. Application Data

(63) Continuation of application No. 12/837,780, filed on Jul. 16, 2010, now Pat. No. 8,741,833.

(51) Int. Cl.
| | | |
|---|---|---|
| *A61K 38/07* | (2006.01) | |
| *A61K 38/00* | (2006.01) | |
| *A61K 31/00* | (2006.01) | |
| *C07K 14/00* | (2006.01) | |
| *A61L 27/22* | (2006.01) | |
| *A61L 27/24* | (2006.01) | |
| *A61L 27/38* | (2006.01) | |
| *C07K 5/103* | (2006.01) | |
| *C07K 7/06* | (2006.01) | |
| *C07K 7/08* | (2006.01) | |

(52) U.S. Cl.
CPC .............. *C07K 14/00* (2013.01); *A61K 38/07* (2013.01); *A61L 27/227* (2013.01); *A61L 27/24* (2013.01); *A61L 27/3804* (2013.01); *A61L 27/3834* (2013.01); *A61L 27/3865* (2013.01); *C07K 5/101* (2013.01); *C07K 7/06* (2013.01); *C07K 7/08* (2013.01); *C07K 14/001* (2013.01); *A61K 38/00* (2013.01); *A61L 2430/12* (2013.01); *C07K 2319/735* (2013.01)

(58) Field of Classification Search
None
See application file for complete search history.

(56) References Cited

U.S. PATENT DOCUMENTS

2008/0095758 A1\*  4/2008  Lee et al. ................... 424/94.63
2009/0162437 A1\*  6/2009  Horii et al. ................... 424/484

FOREIGN PATENT DOCUMENTS

| JP | 2009286767 | 12/2009 |
| WO | 2008039483 A2 | 4/2008 |
| WO | WO2008113030 A2 \* | 9/2008 |

OTHER PUBLICATIONS

Semino, "Self-assembling peptides: from Bio-inspired Materials to bone regeneration," J. Dent. Res. 87(7): 606-616 (2008).\*
Caplan et al., "Control of self-assembling oligopeptide matrix formation through systematic variation of amino acid sequence," Biomat. 23:219-227 (2002).\*
Haines-Butterick et al., "Controlling hydrogelation kinetics by peptide design for three-dimensional encapsulation and injectable delivery of cells," PNAS 104:7791-7796 (2007).\*

\* cited by examiner

*Primary Examiner* — Julie Ha
*Assistant Examiner* — Kristina M Hellman
(74) *Attorney, Agent, or Firm* — Elmore Patent Law Group, P.C.; Mahreen Chaudhry Hoda; Carolyn S. Elmore

(57) ABSTRACT

The invention relates to a novel class of self-assembling peptides, compositions thereof, methods for the preparation thereof and methods of use thereof. The invention also encompasses methods for tissue regeneration, increasing the production of extracellular matrix proteins, and methods of treatment comprising administering self-assembling peptides.

11 Claims, 12 Drawing Sheets

Vertical view

Horizontal view

Periodontal ligament fibroblasts    Gingival fibroblasts vPDS_9 vYIG_9 vIKV_9

Periodontal ligament fibroblasts        Gingival fibroblasts

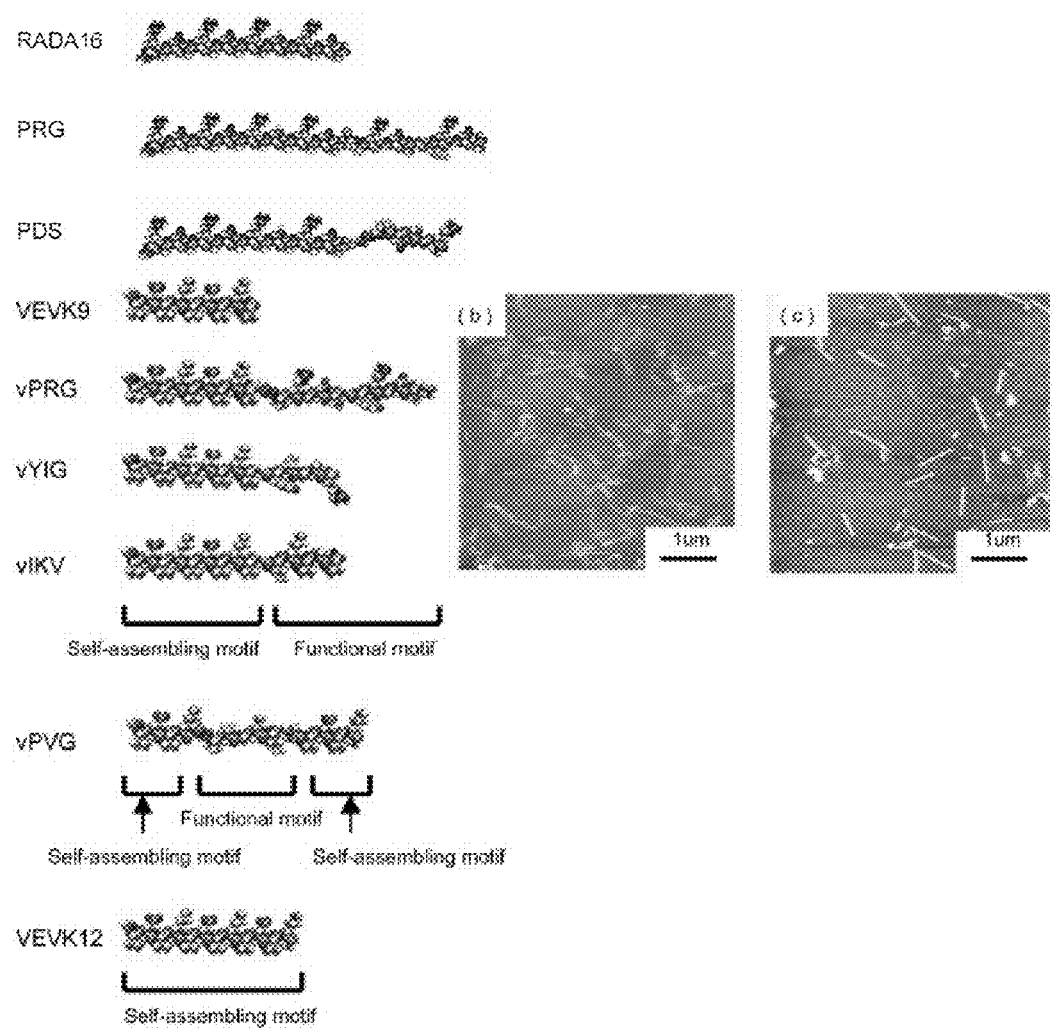
FIGs. 11A, B and C

SEQUENCE LISTING

```
<160> NUMBER OF SEQ ID NOS: 84

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Val Glu Val Lys
 1

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Val Glu Val Lys Val Glu Val Lys Val
 1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Val Glu Val Lys Val Glu Val Lys Val Glu Val Lys
 1               5                   10

<210> SEQ ID NO 4
<211> LENGTH: 5
<212> TYPE: PRT
<213> ORGANISM: Unknown
<220> FEATURE:
<223> OTHER INFORMATION: Mammalian

<400> SEQUENCE: 4

Pro Asp Gly Ser Arg
 1               5

<210> SEQ ID NO 5
<211> LENGTH: 5
<212> TYPE: PRT
<213> ORGANISM: Unknown
<220> FEATURE:
<223> OTHER INFORMATION: Mammalian

<400> SEQUENCE: 5

Tyr Ile Gly Ser Arg
 1               5

<210> SEQ ID NO 6
<211> LENGTH: 5
<212> TYPE: PRT
```

```
<213> ORGANISM: Unknown
<220> FEATURE:
<223> OTHER INFORMATION: Mammalian

<400> SEQUENCE: 6

Ile Lys Val Ala Val
1               5

<210> SEQ ID NO 7
<211> LENGTH: 3
<212> TYPE: PRT
<213> ORGANISM: Unknown
<220> FEATURE:
<223> OTHER INFORMATION: Mammalian

<400> SEQUENCE: 7

Leu Arg Glu
1

<210> SEQ ID NO 8
<211> LENGTH: 10
<212> TYPE: PRT
<213> ORGANISM: Unknown
<220> FEATURE:
<223> OTHER INFORMATION: Mammalian

<400> SEQUENCE: 8

Arg Asn Ile Ala Glu Ile Ile Lys Asp Ile
1               5                   10

<210> SEQ ID NO 9
<211> LENGTH: 7
<212> TYPE: PRT
<213> ORGANISM: Unknown
<220> FEATURE:
<223> OTHER INFORMATION: Mammalian

<400> SEQUENCE: 9

Arg Tyr Val Val Leu Pro Arg
1               5

<210> SEQ ID NO 10
<211> LENGTH: 6
<212> TYPE: PRT
<213> ORGANISM: Unknown
<220> FEATURE:
<223> OTHER INFORMATION: Mammalian

<400> SEQUENCE: 10

Leu Gly Thr Ile Pro Gly
1               5

<210> SEQ ID NO 11
<211> LENGTH: 6
<212> TYPE: PRT
<213> ORGANISM: Unknown
<220> FEATURE:
<223> OTHER INFORMATION: Mammalian

<400> SEQUENCE: 11

Pro Val Gly Leu Ile Gly
1               5

<210> SEQ ID NO 12
<211> LENGTH: 7
<212> TYPE: PRT
<213> ORGANISM: Unknown
```

```
<220> FEATURE:
<223> OTHER INFORMATION: Mammalian

<400> SEQUENCE: 12

Gly Pro Val Gly Leu Ile Gly
 1               5

<210> SEQ ID NO 13
<211> LENGTH: 5
<212> TYPE: PRT
<213> ORGANISM: Unknown
<220> FEATURE:
<223> OTHER INFORMATION: Mammalian

<400> SEQUENCE: 13

Pro Arg Gly Asp Ser
 1               5

<210> SEQ ID NO 14
<211> LENGTH: 5
<212> TYPE: PRT
<213> ORGANISM: Unknown
<220> FEATURE:
<223> OTHER INFORMATION: Mammalian

<400> SEQUENCE: 14

Tyr Arg Gly Asp Ser
 1               5

<210> SEQ ID NO 15
<211> LENGTH: 11
<212> TYPE: PRT
<213> ORGANISM: Unknown
<220> FEATURE:
<223> OTHER INFORMATION: Mammalian

<400> SEQUENCE: 15

Pro Arg Gly Asp Ser Gly Tyr Arg Gly Asp Ser
 1               5                  10

<210> SEQ ID NO 16
<211> LENGTH: 6
<212> TYPE: PRT
<213> ORGANISM: Unknown
<220> FEATURE:
<223> OTHER INFORMATION: Mammalian

<400> SEQUENCE: 16

Pro Val Gly Leu Ile Gly
 1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Arg Ala Asp Ala
 1

<210> SEQ ID NO 18
<211> LENGTH: 16
<212> TYPE: PRT
<213> ORGANISM: Artificial Sequence
<220> FEATURE:
```

<223> OTHER INFORMATION: Synthetic

<400> SEQUENCE: 18

Arg Ala Asp Ala Arg Ala Asp Ala Arg Ala Asp Ala Arg Ala Asp Ala
1               5                   10                  15

<210> SEQ ID NO 19
<211> LENGTH: 6
<212> TYPE: PRT
<213> ORGANISM: Unknown
<220> FEATURE:
<223> OTHER INFORMATION: Mammalian

<400> SEQUENCE: 19

Pro Val Gly Leu Ile Gly
1               5

<210> SEQ ID NO 20
<211> LENGTH: 16
<212> TYPE: PRT
<213> ORGANISM: Artificial Sequence
<220> FEATURE:
<223> OTHER INFORMATION: Synthetic

<400> SEQUENCE: 20

Arg Ala Asp Ala Arg Gly Asp Ala Arg Ala Asp Ala Arg Gly Asp Ala
1               5                   10                  15

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Arg Ala Asp Ala Arg Ala Asp Ala
1               5

<210> SEQ ID NO 22
<211> LENGTH: 16
<212> TYPE: PRT
<213> ORGANISM: Artificial Sequence
<220> FEATURE:
<223> OTHER INFORMATION: Synthetic

<400> SEQUENCE: 22

Arg Ala Arg Ala Asp Ala Asp Ala Arg Ala Arg Ala Asp Ala Asp Ala
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Arg Ala Arg Ala Asp Ala Asp Ala
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic

```
<400> SEQUENCE: 24

Ala Glu Ala Lys Ala Glu Ala Lys Ala Glu Ala Lys Ala Glu Ala Lys
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Ala Glu Ala Lys Ala Glu Ala Lys
1               5

<210> SEQ ID NO 26
<211> LENGTH: 15
<212> TYPE: PRT
<213> ORGANISM: Artificial Sequence
<220> FEATURE:
<223> OTHER INFORMATION: Synthetic

<400> SEQUENCE: 26

Arg Ala Glu Ala Arg Ala Glu Ala Arg Ala Glu Ala Arg Ala Glu
1               5                   10                  15

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Arg Ala Glu Ala Arg Ala Glu Ala
1               5

<210> SEQ ID NO 28
<211> LENGTH: 16
<212> TYPE: PRT
<213> ORGANISM: Artificial Sequence
<220> FEATURE:
<223> OTHER INFORMATION: Synthetic

<400> SEQUENCE: 28

Lys Ala Asp Ala Lys Ala Asp Ala Lys Ala Asp Ala Lys Ala Asp Ala
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Lys Ala Asp Ala Lys Ala Asp Ala
1               5

<210> SEQ ID NO 30
<211> LENGTH: 16
<212> TYPE: PRT
<213> ORGANISM: Artificial Sequence
<220> FEATURE:
<223> OTHER INFORMATION: Synthetic
```

```
<400> SEQUENCE: 30

Ala Glu Ala Glu Ala His Ala His Ala Glu Ala Glu Ala His Ala His
1               5                   10                  15

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Ala Glu Ala Glu Ala His Ala His
1               5

<210> SEQ ID NO 32
<211> LENGTH: 16
<212> TYPE: PRT
<213> ORGANISM: Artificial Sequence
<220> FEATURE:
<223> OTHER INFORMATION: Synthetic

<400> SEQUENCE: 32

Phe Glu Phe Glu Phe Lys Phe Lys Phe Glu Phe Glu Phe Lys Phe Lys
1               5                   10                  15

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Phe Glu Phe Lys Phe Glu Phe Lys
1               5

<210> SEQ ID NO 34
<211> LENGTH: 16
<212> TYPE: PRT
<213> ORGANISM: Artificial Sequence
<220> FEATURE:
<223> OTHER INFORMATION: Synthetic

<400> SEQUENCE: 34

Leu Glu Leu Glu Leu Lys Leu Lys Leu Glu Leu Glu Leu Lys Leu Lys
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Leu Glu Leu Glu Leu Lys Leu Lys
1               5

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36
```

Ala Glu Ala Glu Ala Lys Ala Lys Ala Glu Ala Glu Ala Lys Ala Lys
1               5                   10                  15

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Ala Glu Ala Glu Ala Glu Ala Glu Ala Lys Ala Lys
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ala Glu Ala Glu Ala Lys Ala Lys
1               5

<210> SEQ ID NO 39
<211> LENGTH: 16
<212> TYPE: PRT
<213> ORGANISM: Artificial Sequence
<220> FEATURE:
<223> OTHER INFORMATION: Synthetic

<400> SEQUENCE: 39

Lys Ala Lys Ala Lys Ala Lys Ala Glu Ala Glu Ala Glu Ala Glu Ala
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Ala Glu Ala Glu Ala Glu Ala Glu Ala Lys Ala Lys Ala Lys Ala Lys
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic

<400> SEQUENCE: 41

Arg Ala Arg Ala Arg Ala Arg Ala Asp Ala Asp Ala Asp Ala Asp Ala
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Ala Asp Ala Asp Ala Asp Ala Asp Ala Arg Ala Arg Ala Arg Ala Arg
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic

<400> SEQUENCE: 43

Asp Ala Asp Ala Asp Ala Asp Ala Arg Ala Arg Ala Arg Ala Arg Ala
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic

<400> SEQUENCE: 44

Ala Asp Ala Asp Ala Asp Ala Asp Ala Arg Ala Arg Ala Arg Ala Arg
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic

<400> SEQUENCE: 45

His Glu His Glu His Lys His Lys His Glu His Glu His Lys His Lys
1               5                   10                  15

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

His Glu His Glu His Lys His Lys
1               5

<210> SEQ ID NO 47
<211> LENGTH: 20
<212> TYPE: PRT
<213> ORGANISM: Artificial Sequence
<220> FEATURE:
<223> OTHER INFORMATION: Synthetic

<400> SEQUENCE: 47

Val Glu Val Glu Val Glu Val Glu Val Glu Val Glu Val Glu Val Glu
1               5                   10                  15

Val Glu Val Glu
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic -continued

```
<400> SEQUENCE: 48

Arg Phe Arg Phe Arg Phe Arg Phe Arg Phe Arg Phe Arg Phe Arg Phe
1               5                   10                  15

Arg Phe Arg Phe
            20

<210> SEQ ID NO 49
<211> LENGTH: 12
<212> TYPE: PRT
<213> ORGANISM: Unknown
<220> FEATURE:
<223> OTHER INFORMATION: Mammalian

<400> SEQUENCE: 49

Ala Ala Ser Ile Lys Val Ala Val Ser Ala Asp Arg
1               5                   10

<210> SEQ ID NO 50
<211> LENGTH: 19
<212> TYPE: PRT
<213> ORGANISM: Unknown
<220> FEATURE:
<223> OTHER INFORMATION: Mammalian

<400> SEQUENCE: 50

Cys Ser Arg Ala Arg Lys Gln Ala Ala Ser Ile Lys Val Ala Val Ser
1               5                   10                  15

Ala Asp Arg

<210> SEQ ID NO 51
<211> LENGTH: 12
<212> TYPE: PRT
<213> ORGANISM: Unknown
<220> FEATURE:
<223> OTHER INFORMATION: Mammalian

<400> SEQUENCE: 51

Lys Ala Phe Asp Ile Thr Tyr Val Arg Leu Lys Phe
1               5                   10

<210> SEQ ID NO 52
<211> LENGTH: 12
<212> TYPE: PRT
<213> ORGANISM: Unknown
<220> FEATURE:
<223> OTHER INFORMATION: Mammalian

<400> SEQUENCE: 52

Thr Ala Gly Ser Cys Leu Arg Lys Phe Ser Thr Met
1               5                   10

<210> SEQ ID NO 53
<211> LENGTH: 4
<212> TYPE: PRT
<213> ORGANISM: Unknown
<220> FEATURE:
<223> OTHER INFORMATION: Mammalian

<400> SEQUENCE: 53

Tyr Val Arg Leu
1

<210> SEQ ID NO 54
<211> LENGTH: 6
<212> TYPE: PRT
```

<213> ORGANISM: Unknown
<220> FEATURE:
<223> OTHER INFORMATION: Mammalian

<400> SEQUENCE: 54

Ile Arg Val Thr Leu Asn
1               5

<210> SEQ ID NO 55
<211> LENGTH: 8
<212> TYPE: PRT
<213> ORGANISM: Unknown
<220> FEATURE:
<223> OTHER INFORMATION: Mammalian

<400> SEQUENCE: 55

Thr Thr Val Lys Tyr Ile Phe Arg
1               5

<210> SEQ ID NO 56
<211> LENGTH: 8
<212> TYPE: PRT
<213> ORGANISM: Unknown
<220> FEATURE:
<223> OTHER INFORMATION: Mammalian

<400> SEQUENCE: 56

Ser Ile Lys Ile Arg Gly Thr Tyr
1               5

<210> SEQ ID NO 57
<211> LENGTH: 13
<212> TYPE: PRT
<213> ORGANISM: Unknown
<220> FEATURE:
<223> OTHER INFORMATION: Mammalian

<400> SEQUENCE: 57

Arg Gln Val Phe Gln Val Ala Tyr Ile Ile Ile Lys Ala
1               5                   10

<210> SEQ ID NO 58
<211> LENGTH: 10
<212> TYPE: PRT
<213> ORGANISM: Unknown
<220> FEATURE:
<223> OTHER INFORMATION: Mammalian

<400> SEQUENCE: 58

Phe Gln Ile Ala Tyr Val Ile Val Lys Ala
1               5                   10

<210> SEQ ID NO 59
<211> LENGTH: 13
<212> TYPE: PRT
<213> ORGANISM: Unknown
<220> FEATURE:
<223> OTHER INFORMATION: Mammalian

<400> SEQUENCE: 59

Gly Gln Leu Phe His Val Ala Tyr Ile Ile Ile Lys Ala
1               5                   10

<210> SEQ ID NO 60
<211> LENGTH: 10
<212> TYPE: PRT
<213> ORGANISM: Unknown

```
<220> FEATURE:
<223> OTHER INFORMATION: Mammalian

<400> SEQUENCE: 60

Phe His Val Ala Tyr Val Leu Ile Lys Ala
 1               5                  10

<210> SEQ ID NO 61
<211> LENGTH: 13
<212> TYPE: PRT
<213> ORGANISM: Unknown
<220> FEATURE:
<223> OTHER INFORMATION: Mammalian

<400> SEQUENCE: 61

Leu Glu Asn Gly Glu Ile Val Ser Leu Val Asn Gly Arg
 1               5                  10

<210> SEQ ID NO 62
<211> LENGTH: 4
<212> TYPE: PRT
<213> ORGANISM: Unknown
<220> FEATURE:
<223> OTHER INFORMATION: Mammalian

<400> SEQUENCE: 62

Asp Gly Glu Ala
 1

<210> SEQ ID NO 63
<211> LENGTH: 4
<212> TYPE: PRT
<213> ORGANISM: Unknown
<220> FEATURE:
<223> OTHER INFORMATION: Mammalian

<400> SEQUENCE: 63

Arg Glu Asp Val
 1

<210> SEQ ID NO 64
<211> LENGTH: 5
<212> TYPE: PRT
<213> ORGANISM: Unknown
<220> FEATURE:
<223> OTHER INFORMATION: Mammalian

<400> SEQUENCE: 64

Gly Val Gly Val Pro
 1               5

<210> SEQ ID NO 65
<211> LENGTH: 6
<212> TYPE: PRT
<213> ORGANISM: Unknown
<220> FEATURE:
<223> OTHER INFORMATION: Mammalian

<400> SEQUENCE: 65

Gly Val Gly Val Ala Pro
 1               5

<210> SEQ ID NO 66
<211> LENGTH: 7
<212> TYPE: PRT
<213> ORGANISM: Unknown
<220> FEATURE:
```

<223> OTHER INFORMATION: Mammalian

<400> SEQUENCE: 66

Pro Phe Ser Ser Thr Lys Thr
1               5

<210> SEQ ID NO 67
<211> LENGTH: 8
<212> TYPE: PRT
<213> ORGANISM: Unknown
<220> FEATURE:
<223> OTHER INFORMATION: Mammalian

<400> SEQUENCE: 67

Ser Lys Pro Pro Gly Thr Ser Ser
1               5

<210> SEQ ID NO 68
<211> LENGTH: 9
<212> TYPE: PRT
<213> ORGANISM: Unknown
<220> FEATURE:
<223> OTHER INFORMATION: Mammalian

<400> SEQUENCE: 68

Ser Asp Pro Gly Tyr Ile Gly Ser Arg
1               5

<210> SEQ ID NO 69
<211> LENGTH: 12
<212> TYPE: PRT
<213> ORGANISM: Unknown
<220> FEATURE:
<223> OTHER INFORMATION: Mammalian

<400> SEQUENCE: 69

Pro Arg Gly Asp Ser Gly Tyr Arg Gly Asp Ser Gly
1               5                   10

<210> SEQ ID NO 70
<211> LENGTH: 7
<212> TYPE: PRT
<213> ORGANISM: Unknown
<220> FEATURE:
<223> OTHER INFORMATION: Mammalian

<400> SEQUENCE: 70

Gly Phe Leu Gly Phe Pro Thr
1               5

<210> SEQ ID NO 71
<211> LENGTH: 7
<212> TYPE: PRT
<213> ORGANISM: Unknown
<220> FEATURE:
<223> OTHER INFORMATION: Mammalian

<400> SEQUENCE: 71

Tyr Gly Pro Asp Ser Gly Arg
1               5

<210> SEQ ID NO 72
<211> LENGTH: 29
<212> TYPE: PRT
<213> ORGANISM: Artificial Sequence
<220> FEATURE:
<223> OTHER INFORMATION: Synthetic -continued

<400> SEQUENCE: 72

Arg Ala Asp Ala Arg Ala Asp Ala Arg Ala Asp Ala Arg Ala Asp Ala
1               5                   10                  15

Gly Gly Pro Arg Gly Asp Ser Gly Tyr Arg Gly Asp Ser
            20                  25

<210> SEQ ID NO 73
<211> LENGTH: 23
<212> TYPE: PRT
<213> ORGANISM: Artificial Sequence
<220> FEATURE:
<223> OTHER INFORMATION: Synthetic

<400> SEQUENCE: 73

Arg Ala Asp Ala Arg Ala Asp Ala Arg Ala Asp Ala Arg Ala Asp Ala
1               5                   10                  15

Gly Gly Pro Asp Ser Gly Arg
            20

<210> SEQ ID NO 74
<211> LENGTH: 27
<212> TYPE: PRT
<213> ORGANISM: Artificial Sequence
<220> FEATURE:
<223> OTHER INFORMATION: Synthetic

<400> SEQUENCE: 74

Arg Ala Asp Ala Arg Ala Asp Ala Arg Ala Asp Ala Arg Ala Asp Ala
1               5                   10                  15

Gly Gly Ser Asp Pro Gly Tyr Ile Gly Ser Arg
            20                  25

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Val Glu Val Lys Val Glu Val Lys Val
1               5

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Val Glu Val Lys Val Glu Val Lys Val Glu Val Lys
1               5                   10

<210> SEQ ID NO 77
<211> LENGTH: 22
<212> TYPE: PRT
<213> ORGANISM: Artificial Sequence
<220> FEATURE:
<223> OTHER INFORMATION: Synthetic

<400> SEQUENCE: 77

Val Glu Val Lys Val Glu Val Lys Val Gly Pro Arg Gly Asp Ser Gly
1               5                   10                  15

```
<210> SEQ ID NO 78
<211> LENGTH: 15
<212> TYPE: PRT
<213> ORGANISM: Artificial Sequence
<220> FEATURE:
<223> OTHER INFORMATION: Synthetic

<400> SEQUENCE: 78

Val Glu Val Lys Val Glu Val Lys Val Gly Pro Asp Ser Gly Arg
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic

<400> SEQUENCE: 79

Val Glu Val Lys Val Glu Val Lys Val Gly Tyr Ile Gly Ser Arg
1               5                   10                  15

<210> SEQ ID NO 80
<211> LENGTH: 21
<212> TYPE: PRT
<213> ORGANISM: Artificial Sequence
<220> FEATURE:
<223> OTHER INFORMATION: Synthetic

<400> SEQUENCE: 80

Val Glu Val Lys Val Glu Val Lys Val Gly Gly Arg Asn Ile Ala Glu
1               5                   10                  15

Ile Ile Lys Asp Ile
            20

<210> SEQ ID NO 81
<211> LENGTH: 15
<212> TYPE: PRT
<213> ORGANISM: Artificial Sequence
<220> FEATURE:
<223> OTHER INFORMATION: Synthetic

<400> SEQUENCE: 81

Val Glu Val Lys Val Glu Val Lys Val Gly Ile Lys Val Ala Val
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic

<400> SEQUENCE: 82

Val Glu Val Lys Gly Pro Val Gly Leu Ile Gly Val Glu Val Lys
1               5                   10                  15

<210> SEQ ID NO 83
<211> LENGTH: 6
<212> TYPE: PRT
<213> ORGANISM: Unknown
<220> FEATURE:
<223> OTHER INFORMATION: Mammalian
```

```
<400> SEQUENCE: 83

Gly Arg Gly Asp Ser Pro
 1               5

<210> SEQ ID NO 84
<211> LENGTH: 24
<212> TYPE: PRT
<213> ORGANISM: Artificial Sequence
<220> FEATURE:
<223> OTHER INFORMATION: Synthetic

<400> SEQUENCE: 84

Arg Ala Asp Ala Arg Ala Asp Ala Arg Ala Asp Ala Pro Val Gly Leu
 1               5                  10                  15

Ile Gly Arg Ala Asp Ala Arg Ala
            20
```

SELF-ASSEMBLING PEPTIDES INCORPORATING MODIFICATIONS AND METHODS OF USE THEREOF

RELATED APPLICATION

This application is a continuation of U.S. application Ser. No. 12/837,780, filed Jul. 16, 2010. The entire teachings of the above application are incorporated herein by reference.

BACKGROUND OF THE INVENTION

The extracellular matrix (ECM) is composed of a diverse set of macromolecules, including both proteins and polysaccharides, which form the three dimensional environment within which cells exist in the body and constitute the space filling material between cells. The ECM can also be organized into a sheet-like layer known as the basal lamina or basement membrane. The ECM consists primarily of molecules that are secreted locally and assemble into a scaffold that stabilizes and supports the physical structure of cell layers and tissues. However, rather than being merely an inert substrate for cell attachment, the ECM constitutes an environment that is rich in biological information. It is recognized that the ECM, and various biomolecules associated with it (e.g., secreted locally or transported to a particular site from elsewhere), exert a significant influence on many aspects of cell behavior and phenotype, regulating processes such as migration and proliferation, influencing cell development and differentiation, and affecting cell shape and function. The structure of the ECM is, in turn, influenced by the cells within it. Not only do these cells secrete many ECM constituents, but they also help to pattern the matrix. Thus it is evident that cell ECM interactions are of vital importance. There remains a need for synthetic compositions and materials for tissue engineering purposes that would allow the creation of a cellular environment that mimics important aspects of the native cellular environment without the disadvantages associated with products derived from natural sources. For applications involving implantation into the body, there remains a particular need for such compositions and materials that elicit no or minimal immune or inflammatory response and for compositions and materials that are degradable within the body. In addition, there remains a need in the art for compositions and materials that would influence cell properties and functions in desirable ways.

It has previously been reported that a class of designer self-assembling peptide scaffolds have wide application including for three-dimensional (3-D) cell culture, drug delivery, regenerative medicine and tissue engineering [1a]-[5a]. The class of self-assembling peptide materials can undergo spontaneous assembly into well-ordered nanofibers and scaffolds, ~10 nm in fiber diameter with pores between 5-200 nm and over 90% water content [6a]. These peptide scaffolds have 3-D nanofiber structures similar to the natural extracellular matrix including collagen. Furthermore, the scaffolds are biodegradable by a variety of proteases in a body with superior biocompatibility with tissue [7a]. Moreover, these scaffolds can be modified and functionalized by direct extension of peptides with known biologically functional peptide motifs to promote specific cellular responses. One family of these peptide scaffolds, functionalized RADA16 has been studied for bone, cartilage, neural regeneration and angiogenesis promotion [8a]-[11a].

In the treatment of periodontal disease, a number of surgical techniques have been developed to regenerate periodontal tissue, including guided tissue regeneration [12a]-[14a], bone grafting [15a], [16a], enamel matrix derivative [17a]-[19a] and the use of growth factors [20a]-[25a]. However, there are concerns associated with use of these animal-derived biomaterials including, for example, the risk of transferring infection agents from animals to human and the difficulty of handling animal-derived biomaterials. Therefore, there remains a need in the art for improved methods for periodontal tissue regeneration.

SUMMARY OF THE INVENTION

The invention relates to a novel class of self-assembling peptides, compositions thereof, methods for the preparation thereof and methods of use thereof. The invention also encompasses methods for tissue regeneration, increasing the production of extracellular matrix proteins, and methods of treatment comprising administering self-assembling peptides.

In one aspect, the invention is directed to a self-assembling peptide comprising the sequence VEVK (SEQ ID NO: 1), wherein the peptide is capable of self-assembly. In additional aspects, the invention encompasses a self-assembling peptide having the sequence VEVKVEVKV (SEQ ID NO: 2) or VEVKVEVKVEVK (SEQ ID NO: 3). The invention also includes a self-assembling peptide comprising the sequence VEVKVEVKV (SEQ ID NO: 2) or VEVKVEVKVEVK (SEQ ID NO: 3).

In another aspect, the invention is directed to a self-assembling peptide wherein the self-assembling peptide comprises:
  a. A first amino acid domain that mediates self-assembly, wherein the first amino acid domain comprises the sequence VEVK (SEQ ID NO:1) and wherein the domain is capable of self-assembly in isolated form; and
  b. A second amino acid domain that does not mediate self-assembly in isolated form.

In some embodiments, the second amino acid domain comprises a biologically active motif. In certain additional aspects, the first amino acid domain is VEVKVEVKV (SEQ ID NO: 2) or VEVKVEVKVEVK (SEQ ID NO: 3). In additional aspects, the biologically active motif is a laminin cell adhesion motif. In yet additional aspects, the second amino acid domain comprises a sequence selected from the group consisting of PDGSR (SEQ ID NO:4), YIGSR (SEQ ID NO: 5), IKVAV (SEQ ID NO: 6), LRE (SEQ ID NO:7), RNIAEIIKDI (SEQ ID NO:8), RYVVLPR (SEQ ID NO: 9), LGTIPG (SEQ ID NO: 10), PVGLIG (SEQ ID NO: 11) and GPVGLIG (SEQ ID NO: 12). In certain embodiments, the second amino acid domain comprises an RGD peptide, such as PRGDS (SEQ ID NO: 13), YRGDS (SEQ ID NO: 14) and PRGDSGYRGDS (SEQ ID NO: 15). In certain additional embodiments, the second amino acid domain comprises a matrix metalloproteinase cleavable substrate. An exemplary matrix metalloproteinase cleavable substrate comprises the sequence PVGLIG (SEQ ID NO: 16).

In yet another embodiment of the invention, the invention is directed to a self-assembling peptide wherein the self-assembling peptide comprises:
  a. A first amino acid domain that mediates self-assembly, wherein the domain comprises alternating hydrophobic and hydrophilic amino acids that are complementary and structurally compatible, wherein said domain self-assembles into a macroscopic structure when present in unmodified form; and b. A second amino acid domain that does not mediate self-assembly in isolated form, wherein the second amino acid domain comprises a biologically active motif, wherein the second amino acid domain comprises a sequence selected from the group consisting of PDGSR (SEQ ID NO: 4), YIGSR (SEQ ID NO: 5), LRE (SEQ ID NO:7), RNIAEIIKDI (SEQ ID NO: 8), RYVVLPR (SEQ ID NO: 9), LGTIPG (SEQ ID NO:10) and GPVGLIG (SEQ ID NO: 12).

In certain aspects, the first amino acid domain of the peptide comprises multiple RADA (SEQ ID NO: 17) peptide subunits, for example, AcN-RADARADARADARADA-CONH2 (SEQ ID NO: 18). In yet another aspect, the first amino acid domain comprises the sequence VEVK (SEQ ID NO: 1), for example, VEVKVEVKV (SEQ ID NO: 2) or VEVKVEVKVEVK (SEQ ID NO: 3).

In yet another aspect, the invention is directed to a method for regenerating a dental tissue in a patient in need thereof comprising administering to the dental tissue of said patient an effective amount of a self-assembling peptide, wherein the self-assembling peptide comprises:
  a. A first amino acid domain that mediates self-assembly, wherein the domain comprises alternating hydrophobic and hydrophilic amino acids that are complementary and structurally compatible, wherein said domain self-assembles into a macroscopic structure when present in unmodified form; and
  b. A second amino acid domain that does not mediate self-assembly in isolated form, wherein the second amino acid domain comprises a biologically active motif.

In some aspects, the dental tissue is periodontal ligament tissue and the self-assembling peptide is administered to the peridontium. In additional aspects, the biologically active motif is a laminin cell adhesion motif, an RGD peptide or a matrix metalloprotease cleavable substrate. In additional embodiments, the second amino acid domain comprises a sequence selected from the group consisting of PDGSR (SEQ ID NO:4), YIGSR (SEQ ID NO:5), IKVAV (SEQ ID NO:6), LRE (SEQ ID NO:7), RNIAEIIKDI (SEQ ID NO:8), RYVVLPR (SEQ ID NO:9), LGTIPG (SEQ ID NO:10), PVGLIG (SEQ ID NO:19), GPVGLIG (SEQ ID NO:12). PRGDS (SEQ ID NO:13), YRGDS (SEQ ID NO:14), PRGDSGYRGDS (SEQ ID NO:15) and PVGLIG (SEQ ID NO:19). In yet another aspect, the first amino acid domain comprises multiple RADA (SEQ ID NO:17) peptide subunits, for example AcN-RADARADARADARADA-CONH2 (SEQ ID NO: 18). In a further aspect, the first amino acid domain comprises the sequence VEVK (SEQ ID NO:1), for example, VEVKVEVKV (SEQ ID NO: 2) or VEVKVEVKVEVK (SEQ ID NO: 3).

The invention also encompasses a method of treating periodontal disease and/or regenerating periodontal ligament tissue in a patient in need thereof comprising administering to the periodontium of said patient an effective amount of a self-assembling peptide, wherein the self-assembling peptide comprises:
  a. A first amino acid domain that mediates self-assembly, wherein the domain comprises alternating hydrophobic and hydrophilic amino acids that are complementary and structurally compatible and wherein said domain self-assembles into a macroscopic structure when present in unmodified form; and
  b. A second amino acid domain that does not mediate self-assembly in isolated form, wherein the second amino acid domain comprises a biologically active motif.

In another embodiment, the invention is a method of increasing extracellular matrix protein production in a tissue comprising administering to said tissue of said patient an effective amount of a self-assembling peptide, wherein the self-assembling peptide comprises:
  a. A first amino acid domain that mediates self-assembly, wherein the domain comprises alternating hydrophobic and hydrophilic amino acids that are complementary and structurally compatible and wherein said first domain self-assembles into a macroscopic structure when present in unmodified form; and
  b. A second amino acid domain that does not mediate self-assembly in isolated form, wherein the second amino acid domain comprises a biologically active motif.

In further embodiments, the extracellular matrix protein is collagen.

The present invention additionally includes a method for regenerating a damaged tissue in a patient in need thereof comprising administering to said patient an effective amount of a self-assembling peptide, wherein the self-assembling peptide comprises:
  a. A first amino acid domain that mediates self-assembly, wherein the domain comprises alternating hydrophobic and hydrophilic amino acids that are complementary and structurally compatible and wherein said first domain self-assembles into a macroscopic structure when present in unmodified form; and
  b. A second amino acid domain that does not mediate self-assembly in isolated form, wherein the second amino acid domain comprises a biologically active motif.

In certain aspects, the first amino acid domain comprises the sequence VEVK (SEQ ID NO:1). Exemplary sequences comprising VEVK (SEQ ID NO: 1) include, for example, VEVKVEVKV (SEQ ID NO: 2) or VEVKVEVKVEVK (SEQ ID NO: 3). In additional embodiments, the patient is suffering from arthritides, a neurological condition, a muscle wasting condition, a neuroendocrine disorder, muscular degeneration, musculotendenous failure, trauma, tissue necrosis, cardiac disorder, surgical resection, growth abnormalities, osteoporosis, fractures, or ischemic damage due to peripheral vascular disease. In a further aspect, the damaged tissue is selected from the group consisting of skeletal, bone, tendon, connective or dental tissue tissues.

In additional aspects, the invention is directed to a scaffold for periodontal tissue regeneration comprising:
  a. A first amino acid domain that mediates self-assembly, wherein the domain comprises alternating hydrophobic and hydrophilic amino acids that are complementary and structurally compatible and wherein said domain self-assembles into a macroscopic structure when present in unmodified form; and
  b. A second amino acid domain that does not mediate self-assembly in isolated form, wherein the second amino acid domain comprises a biologically active motif.

In some aspects, the biologically active motif is a laminin cell adhesion motif, an RGD peptide or a matrix metalloprotease cleavable substrate. In additional aspects, the second amino acid domain comprises a sequence selected from the group consisting of PDGSR (SEQ ID NO: 4), YIGSR (SEQ ID NO: 5), IKVAV (SEQ ID NO: 6), LRE (SEQ ID NO: 7), RNIAEIIKDI (SEQ ID NO: 8), RYVVLPR (SEQ ID NO: 9), LGTIPG (SEQ ID NO: 10), PVGLIG (SEQ ID NO: 19), GPVGLIG (SEQ ID NO: 12). PRGDS (SEQ ID NO: 13), YRGDS (SEQ ID NO: 14), PRGDSGYRGDS (SEQ ID NO: 15) and PVGLIG (SEQ ID NO: 19). In yet another aspect, the first amino acid domain comprises multiple RADA (SEQ ID NO: 17) peptide subunits, for example AcN-RADARADARADARADA-CONH2 (SEQ ID NO: 18). In a further aspects, the first amino acid domain comprises the sequence VEVK (SEQ ID NO: 1) peptide subunits, for example, VEVKVEVKV (SEQ ID NO: 2) or VEVKVEVKVEVK (SEQ ID NO: 3).

In an additional embodiment, the invention is directed to a method of treating periodontal disease comprising administering to a patient in need thereof a scaffold for periodontal tissue regeneration comprising:
 a. A first amino acid domain that mediates self-assembly, wherein the domain comprises alternating hydrophobic and hydrophilic amino acids that are complementary and structurally compatible and wherein said domain self-assembles into a macroscopic structure when present in unmodified form; and
 b. A second amino acid domain that does not mediate self-assembly in isolated form, wherein the second amino acid domain comprises a biologically active motif.

In additional aspects, the method further comprises administering a solid biomaterial.

The invention also encompasses a syringe having two compartments, wherein the first compartment comprises a peptide solution and the second compartment comprises a gelation fluid, wherein the peptide solution is an aqueous solution comprising a self assembling peptide wherein the peptide comprises:
 a. A first amino acid domain that mediates self-assembly, wherein the domain comprises alternating hydrophobic and hydrophilic amino acids that are complementary and structurally compatible and wherein said domain self-assembles into a macroscopic structure when present in unmodified form; and
 b. A second amino acid domain that does not mediate self-assembly in isolated form, wherein the second amino acid domain comprises a biologically active motif.

The invention also encompasses a macroscopic scaffold comprising a plurality self-assembling peptides wherein said peptides comprise the sequence VEVK (SEQ ID NO: 1).

The invention additionally encompasses a macroscopic scaffold comprising a plurality self-assembling peptides wherein said peptides comprise:
 a. A first amino acid domain that mediates self-assembly, wherein the domain comprises alternating hydrophobic and hydrophilic amino acids that are complementary and structurally compatible and wherein said domain self-assembles into a macroscopic structure when present in unmodified form; and
 b. A second amino acid domain that does not mediate self-assembly in isolated form, wherein the second amino acid domain comprises a biologically active motif; wherein said scaffold further comprises living cells attached to its surface or encapsulated within the scaffold.

In certain embodiments, the invention is a macroscopic scaffold wherein the cells on the surface of the scaffold or encapsulated within the scaffold are periodontal ligament fibroblasts. In yet another aspect, the invention is a macroscopic scaffold wherein the first amino acid domain comprises the sequence VEVK (SEQ ID NO:1) and optionally wherein the cells are selected from the group consisting of osteoblasts, cementoblasts, bone marrow cells, fibroblasts, periodontal ligament fibroblasts, mesenchymal cells, mesenchymal stem cells, adipose derived cells, adipose derived stem cells, periodontal ligament stem cells, dental pulp stem cells, stem cells from exfoliated deciduous teeth and embryonic stem cells. In a further embodiment, the cells are periodontal ligament fibroblasts.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 11A shows molecular models of the indicated functionalized peptides.

FIG. 11B and C shows AFM images of VEVK12(b) and vPVG_vPRG_9(c).

DETAILED DESCRIPTION OF THE INVENTION

Figure 1:
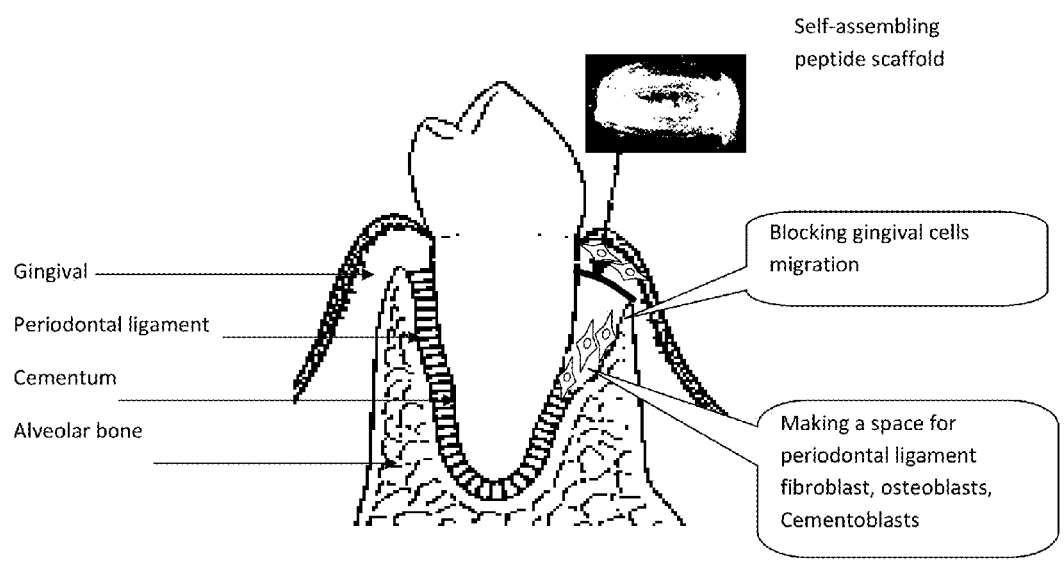
FIG. 1 is a drawing showing the tooth, gingival, periodontal ligament, cementum and alveolar bone.

A description of preferred embodiments of the invention follows.

The words "a" or "an" are meant to encompass one or more, unless otherwise specified. For example, the term "a peptide" encompass one or more peptides unless indicated otherwise.

The term "self-assembly" is a process of molecules or peptides forming regular shaped structures or aggregates in response to conditions in the environment, such as when added to an aqueous medium.

The term "self-assembling peptide" refers to a peptide comprising a self-assembling motif. Self-assembling peptides are peptides that are capable of self-assembly into structures including, but not limited to, macroscopic membranes, nanostructures and the like. Various self-assembling peptides and methods for preparation thereof have been described previously, for example in, U.S. Pat. Nos. 5,670,483, 5,955,343, 6,368,877, 7,098,028, and 7,449,180 and U.S. Patent Application Publication Nos. 2002/0160471, 2005/0181973 and 2007/0203062, the contents of each of which are herein incorporated by reference.

The term "self-assembling motif" refers to a peptide sequence or motif capable of self-assembly.

The term "ionic self-assembling peptide" refers to a self-assembling peptide comprising an alternating sequence of hydrophobic amino acids and hydrophilic amino acids, wherein said hydrophilic amino acids are charged amino acids. In some embodiments, the ionic self-assembling peptide comprises an alternating sequence of hydrophobic amino acids and hydrophilic amino acids, wherein said hydrophilic amino acids are acidic or basic amino acids. Ionic, self-assembling peptides have been described for example in U.S. Pat. No. 5,670,483.

As used herein, the term "amino acid" encompasses a naturally or non-naturally occurring amino acid. Non-naturally occurring amino acids are also referred to herein as "non-natural amino acids." Naturally occurring amino acids are also referred to herein as "natural amino acids." Natural amino acids are represented by their well-known single-letter designations: A for alanine, C for cysteine, D for aspartic acid, E for glutamic acid, F for phenylalanine, G for glycine, H for histidine, I for isoleucine, K for lysine, L for leucine, M for methionine, N for asparagines, P for proline, Q for glutamine, R for arginine, S for serine, T for threonine, V for valine, W for tryptophan and Y for tyrosine.

The term "physiologic pH" is a pH of about 7.

The term "macroscopic" means having dimensions large enough so as to be visible under magnification of 10-fold or less. A macroscopic structure can be two-dimensional or three-dimensional. The terms "macroscopic structure" and "macroscopic material" are used interchangeably herein.

A "biologically active peptide motif" or "biologically active motif" or "biologically active domain" is a peptide motif that induces a phenotypic response or change in an appropriate cell type when the cell is contacted with the peptide comprising the biologically active motif. Biologically active motifs have been described, for example, U.S. Pat. No. 7,713,923, the contents of which are expressly incorporated by reference herein. In some aspects, a biologically active motif is a motif found in a naturally occurring protein. The biologically active peptide motif can be present in isolated form or as part of a larger polypeptide or other molecule. The ability of the peptide to elicit the response can be determined, for example, by comparing the response in the absence of the peptide (e.g., by mutating or removing the peptide when normally present within a larger polypeptide). In some embodiments of the invention, phenotypic responses or changes include, but are not limited to, enhancement of cell spreading, attachment, adhesion, proliferation, secretion of an extracellular matrix (ECM) molecule, or expression of a phenotype characteristic of a particular differentiated cell type.

As used herein, "isolated" means 1) separated from at least some of the components with which it is usually associated in nature or which naturally accompany it; 2) prepared or purified by a process that involves the hand of man; and/or 3) not occurring in nature.

According to the present invention, a "peptide", "polypeptide", or "protein" comprises a sequence of at least two amino acids linked together by peptide bonds. Amino acid sequences and formulae described herein are written according to convention such that the sequences are read from left to right wherein the left corresponds to the N-terminal end and the right corresponds to the C-terminal end.

An amino acid domain that does not self-assemble is an amino acid domain that does not self-assemble when present as an isolated peptide (i.e., when not joined or linked to a self-assembling peptide) under conditions (e.g., ionic concentration, peptide concentration, pH, temperature) that would result in self-assembly of an unmodified self-assembling peptide as described below. By "does not self-assemble", is meant that the amino acid domain or peptide does not form nanofilaments or nanofibers, does not form a macroscopic structure, or typically, does not form either β-sheets, nanofibers, or a macroscopic structure.

"Treating" or "treatment" includes the administration of the compositions, compounds or agents of aspects of the present invention to prevent or delay the onset of the symptoms, complications, or biochemical indicia of a disease, alleviating or ameliorating the symptoms and/or or arresting or inhibiting further development of the disease, condition, or disorder.

A "therapeutically effective amount" is an amount which, alone or in combination with one or more other active agents, can control, decrease, inhibit, ameliorate, prevent or otherwise affect one or more symptoms of a disease or condition to be treated.

An "effective amount" is an amount which, alone or in combination with one or more other active agents is sufficient to achieve the indicated objective. For example, an "effective amount" of an agent in the context of regenerating tissue means that the amount of the agent is sufficient to result in tissue regeneration.

Self-assembling peptides

As described above, the present invention is directed to methods and compositions comprising self-assembling peptides comprising a first amino acid domain capable of self-assembly when present in unmodified form and a second amino acid domain that does not self-assemble in isolated or unmodified form. Self-assembling peptides are peptides that are capable of self-assembly into structures include, but are not limited to, macroscopic membranes, nanostructures and the like. Such self-assembling peptides and exemplary peptides that can be used in the first amino acid domain of a peptide described herein have been described, for example, in U.S. Pat. Nos. 5,670,483, 5,955,343, 6,368,877, 7,098,028, and 7,449,180 and U.S. Patent Application Publication Nos. 2005/0181973, 2007/0203062 and 2009/0162437A1, the contents of each of which are expressly incorporated by reference herein.

Numerous self-assembling self-complementary peptides have been designed by changing the amino acid sequence and following a periodic pattern. In certain embodiments, the self-assembling peptides assume regular secondary structures, for example, β-sheet structures, in solution (e.g., aqueous solution). This may be attributed to the fact that peptides contain two distinct surfaces, one hydrophilic and the other hydrophilic and form complementary ionic bonds with regular repeats on the hydrophilic surface. The side-chains of the peptides partition into two faces, a polar face made up of charged ionic side chains and a nonpolar face made up of hydrophobic groups. The ionic side chains are self-complementary to one another in that the positively charged and negatively charged amino acid residues can form complementary ionic pairs. The complementary ionic sides have been classified into several moduli, i.e., modulus I, II, III, IV, etc., and mixed moduli. Modulus I peptides are those wherein the ionic residues alternate with one positively and one negatively charged residue (−+−+−+−+). Modulus II peptides are those wherein the ionic residues alternate with two positively and two negatively charged residues (−−++−−++). Modulus IV peptides are those wherein the ionic residues alternate with four positively and two negatively charged residues (−−−−++++).

Peptides that self-assemble in isolated form may be referred to herein as unmodified self-assembling peptides to distinguish them from "modified" or "functionalized" self assembling peptides (which, in addition to a first amino acid domain that self-assembles in isolated form, further comprise one or more additional amino acid domains that do not self-assemble when present in isolated form). Modified self-assembling peptides and hydrogels formed therefrom are also described herein as "functionalized."

In one embodiment, the first amino acid domain which is capable of self-assembly has alternating hydrophobic and hydrophilic amino acids. In some aspects, the first amino acid domain which is capable of self-assembly is at least 8 amino acids in length. The optimal length of the peptides varies depending on the amino acid composition.

Peptides that can form ionized pairs between their hydrophilic side chains are referred to as "complementary" peptides. Peptides which can maintain a constant distance upon pairing are referred to as "structurally compatible." Peptides meeting the criteria described above are expected to self-assemble into macroscopic membranes in homogenous peptide solutions and are referred to herein as "self-complementary peptides" or "peptides having alternating hydrophobic and hydrophilic amino acids." Such macroscopic membranes can also be formed of heterogenous mixtures of peptides (each of which alone would not form membranes) if the peptides are complementary and structurally compatible to each other. An example of a heterogenous mixture of peptides is a mixture of (Lys-Ala-Lys-Ala)$_4$ and (Glu-Ala-Glu-Ala)$_4$ or a mixture of (Lys-Ala-Lys-Ala)$_4$ and (Ala-Asp-Ala-Asp)$_4$. Macroscopic membranes do not form in water but form in solution comprising salt. The presence of monovolent metal cations induces membrane formation but divalent cations primarily induce unstructured aggregates. These macroscopic membranes are stable in a variety of aqueous solutions including, but not limited to, water, phosphate buffered saline (PBS), serum and ethanol.

It is noted that in certain embodiments of the invention a group or radical such as an acyl group (RCO—, where R is an organic group), e.g., an acetyl group (CH3CO—) is present at the N terminus of the peptides in order to neutralize an extra charge positive that may otherwise be present (e.g., a charge not resulting from the side chain of the N-terminal amino acid). Similarly, a group such as an amine group (NH2) may be used to neutralize an extra negative charge that may otherwise be present at the C terminus (e.g., a charge not resulting from the side chain of C-terminal amino acid), thus converting the C terminus into an amide (—CONH2). While not wishing to be bound by any theory, the neutralization of charges on the terminal N and C molecules may facilitate self-assembly. It is well within the purview of the person of ordinary skill in the art to select other suitable groups.

The self-complementary peptides self-assemble into various macroscopic structures upon exposure to a sufficient concentration of ions (including, for example, monovalent cations) to form macroscopic porous matrices. These matrices can assume various physical forms, including, but not limited to, ribbons, tape-like structures, two and three-dimensional scaffolds and the like. In one embodiment, the matrices are comprised of interwoven filaments about 10 to about 20 nm in diameter with a pore size of about 50 to about 100 nm in diameter. Detailed methods for the preparation of macroscopic structure have been described in U.S. Pat. Nos. 5,670,483, 5,955,343, and 6,368,877, the contents of each of which are expressly incorporated by reference herein. Self-assembly of the self-complementary peptides can be initiated by dissolving the peptides in a solution that is substantially free of monovalent cations or contains only a low concentration of such ions (for example, less than about 10 nM) followed by the addition of an ionic solute to a peptide solution or by a changing the pH of the solution. Assembly of the self-complementary peptides into macroscopic structures can also be initiated by the addition of the peptides to a solution comprising monovalent ions in a concentration sufficient to initiate self-assembly.

In one embodiment the self-assembling peptides that are expected to form macroscopic structures in homogenous mixtures are represented by one of the following formulae:

 (Formula I)

 (Formula II)

wherein:
Φ,Ψ, and Γ represent neutral, positively and negatively charged amino acids, respectively, which determine the composition and structure,
i, j, k and t are integers and denote variable numbers; and
n represents the numbers of repeating units which also determines the length of oligopeptides.

As mentioned above, in some embodiments, self-assembling peptides self-assemble to form a network of nanofibers, resulting in hydrogels of water content higher than 99%, when dissolved water in a range of 1-10 mg/ml. The nanofiber network can give rise to hydrogel formation, creating a macroscopic structure preferably of a size that can be observed with the naked eye and can be three-dimensional. The peptides forming the macroscopic structure can contain between 8 and 200 amino acids, 8 to 64 amino acids, 8 to 36 amino acids, or 8 to 16 amino acids, inclusive. The concentration of the peptides prior to self-assembly can range, for example, between about 0.01% (0.1 mg/ml) and about 99.99% (999.9 mg/ml), inclusive. In addition, the concentration of the peptides prior to self-assembly can be between about 0.1% (1 mg/ml) and about 10% (100 mg/ml), inclusive, particularly for cell culture and/or therapeutic applications. In certain embodiments of the invention, the concentration of the peptides prior to self-assembly is between about 0.1% (1 mg/ml) and about 5% (50 mg/ml), inclusive, or between about 0.5% (5 mg/ml) and about 5% (50 mg/ml), inclusive. In certain embodiments, the concentration of the peptides prior to self-assembly is about 5 mg/ml, about 10 mg/ml, about 15 mg/ml, or about 20 mg/ml.

If desired, peptide scaffolds can be formed with a predetermined shape or volume. To form a scaffold with a desired geometry or dimension, an aqueous peptide solution can be placed in a pre-shaped casting mold, and the peptides induced to self-assemble into a scaffold by the addition of an ion, as described herein. Alternatively, the ion can be added to the peptide solution shortly before placing the solution into the mold, provided that care is taken to place the solution into the mold before substantial assembly occurs. The resulting material characteristics, time required for assembly, and geometry and dimensions of the macroscopic peptide scaffold are governed by parameters including the concentration and amount of peptide solution that is applied, the concentration of ion used to induce assembly of the scaffold, the pH, the particular self-assembling peptide sequence, and the dimensions of the casting apparatus. Where the peptide structure or scaffold is to be implanted into the body, the shape can be selected based upon the intended implantation site. The scaffold can exist as a thin layer, e.g., coating the bottom of a conventional tissue culture or floating in a solution, according to various embodiments of the invention. The layer can, for example, be several microns thick, e.g., 10 microns, 10-50 microns, 50-100 microns, 100-200 microns, etc. The layer can, for example, comprise multiple beta-sheets layers. Self-assembled nanoscale scaffolds can be formed with varying degrees of stiffness or elasticity. The peptide scaffolds typically have a low elastic modulus, e.g., in the range of 1-10 kPa as measured in a standard cone-plate rheometer.

Specific non-limiting examples of self-complementary peptides that can be used in the compositions and methods as described herein are listed in Table 1 below:

TABLE 1

| Name | Sequence (from N-terminus to C-terminus) | Modulus | SEQ ID NO: |
|---|---|---|---|
| RADA-16-1 | n-RADARADARADARADA-c | I | 18 |
| RGDA 16-1 | n-RADARGDARADARGDA-c | II | 20 |
| RADA 8-I | RADARADA-c | I | 21 |
| RAD16-II | n-RARADADARARADADA-c | II | 22 |
| RAD8-II | n-RARADADA-c | II | 23 |
| EAKA16-I | n-AEAKAEAKAEAKAEAK-c | I | 24 |
| EAKA8-I | n-AEAKAEAK-c | I | 25 |
| RAEA16-I | n-RAEARAEARAEARAEA- | I | 26 |
| RAEA8-I | n-RAEARAEA-c | I | 27 |
| KADA16-I | n-KADAKADAKADAKADA-c | I | 28 |
| KADA8-I | n-KADAKADA-c | I | 29 |
| EAH16-II | n-AEAEAHAHAEAEAHAH-c | II | 30 |
| EAH8-II | n-AEAEAHAH-c | II | 31 |
| EFK16-II | n-FEFEFKFKFEFEFKFK-c | II | 32 |
| EFK8-II | n-FEFKFEFK-c | I | 33 |
| ELK16-II | n-LELELKLKLELELKLK-c | II | 34 |
| ELK8-II | n-LELELKLK-c | II | 35 |
| EAK16-II | n-AEAEAKAKAEAEAKAK-c | II | 36 |
| EAK12 | n-AEAEAEAEAKAK- c | IV/II | 37 |
| EAK8-II | n-AEAEAKAK-c | II | 38 |
| KAE16-IV | n-KAKAKAKAEAEAEAEA-c | IV | 39 |

TABLE 1-continued

| Name | Sequence (from N-terminus to C-terminus) | Modulus | SEQ ID NO: |
|---|---|---|---|
| EAK16-IV | n-AEAEAEAEAKAKAKAK-c | IV | 40 |
| RAD16-IV | n-RARARARADADADADA-C | IV | 41 |
| DAR16-IV | n-ADADADADARARARAR-c | IV | 42 |
| DAR16-IV* | n-DADADADARARARARA-c | IV | 43 |
| DAR32-IV | n-(ADADADADARARARAR)-c | IV | 44 |
| EHK16 | n-HEHEHKHKHEHEHKHK-c | N/A | 45 |
| EHK8-I | n-HEHEHKHK-c | N/A | 46 |
| VE20* | n-VEVEVEVEVEVEVEVEVEVE-c | N/A | 47 |
| RF20* | n-RFRFRFRFRFRFRFRFRFRF-c | N/A | 48 |
| VEVK9 | n-VEVKVEVKV-c | | 2 |
| VEVK12 | n-VEVKVEVKVEVK-c | | 3 |

*These peptides form a β-sheet when incubated in a solution containing NaCl, however they have not been observed to self-assemble to form macroscopic structures.

VEVK9 and VEVK12 are described in more detail below. Other examples of self-complementary peptides are described, for example, in U.S. Pat. Nos. 5,670,483, 5,955,343, 6,368,877 and U.S. Patent Application Publication No 20090162437A1, the contents of each of which are expressly incorporated herein.

In additional, the amino acids of the self-assembling peptides are natural amino acids. In another embodiment, the amino acids of the self-assembling motif comprise a non-natural amino acid. In yet another aspect, the peptides may include L-amino acids, D-amino acids, natural amino acids, nonnatural amino acids, or a combination thereof. Numerous classes of non-natural amino acids including D-amino acids have been described (Luo et al. (2008), PLoS ONE 3(5): e2364. doi:10.1371/journal.pone.0002364, the contents of which are incorporated by reference herein). An exemplary, non-natural amino acid is hyroxy-proline. If L-amino acids are present in the scaffold, degradation produces amino acids that may be reused, e.g., by cells in culture or by cells in a host tissue. The peptides can be chemically synthesized or purified from natural or recombinant sources, and the amino- and carboxy-termini of the peptides may be protected or not protected. The peptide scaffold can be formed from one or more distinct molecular species of peptides which are complementary and structurally compatible with each other. Peptides containing mismatched pairs, such as the repulsive pairing of two similarly charged residues from adjacent peptides, can also form structures if the disruptive force is dominated by stabilizing interactions between the peptides.

Peptides comprising the amino acid sequence VEVK (SEQ ID NO: 1)

As described above, several self-assembling peptides have been described in the literature. These self-assembling peptides undergo spontaneous assembly into structures such as nanofibers and macroscopic scaffolds. Exemplary peptides are complementary and structurally compatible and are composed of repeating units of alternating hydrophilic and hydrophobic amino acids, in which the charged residues can include alternating positive and negative charges. An exemplary self-assembling peptide is RADA-16-I (Ac-RA- DARADARADARADA-CONH2 (SEQ ID NO: 18). Functionalized scaffolds comprising RADA-16-I have been described as having utility in bone, cartilage and neural regeneration [6b-10b]. Functionalized RADA-16-1 can result in a relatively long peptide sequence. It may, under some circumstances, be desirable to manufacture a shorter peptide scaffold.

The formation of self-assembling peptide scaffolds and properties thereof are influenced by many factors, including the level of hydrophobicity. Therefore, in addition to ionic complementary interactions, the extent of hydrophobic residues can influence the mechanical properties of the scaffolds and the rate of self-assembly. Higher hydrophobicity of a peptide corresponds to a shorter length of peptide required for self-assembly and easier scaffold properties. Natural amino acids that are hydrophobic include alanine, valine, isoleucine, leucine, tyrosine, phenylalanine, and tryptophan.

In some embodiments, the present invention is directed to self-assembling peptides comprising the amino acid sequence VEVK (SEQ ID NO: 1). In certain embodiments, the self-assembling peptide comprising the sequence VEVK (SEQ ID NO: 1) is 7 to 16 amino acid in length, 8 to 14 amino acids in length, or 9 to 12 amino acids in length. Non-limiting examples of peptides comprising VEVK (SEQ ID NO: 1) are VEVKVEVKV (SEQ ID NO: 2) and VEVKVEVKVEVK (SEQ ID NO: 3). In a further embodiment, the amino acid comprising VEVK (SEQ ID NO:1) comprises the sequence VEVKVEVKV (SEQ ID NO: 2) or VEVKVEVKVEVK (SEQ ID NO: 3).

In additional aspects, the invention is a self-assembling peptide that comprises:
  a. A first amino acid domain that mediates self-assembly, wherein the first amino acid domain comprises the sequence VEVK (SEQ ID NO:1) and wherein the peptide is capable of self-assembly in isolated form; and
  b. A second amino acid domain that does not mediate self-assembly in isolated form, wherein the second amino acid domain comprises a biologically active motif.

Exemplary biologically active motifs have been described in the scientific and patent literature, including for example in U.S. Patent Application Publication Nos. 20090162437A1, 20050181973 and 20070203062 and Gelain et al. (2006). PLoS ONE 1(1): e119. doi:10.1371/journal.pone.0000119, the contents of which are expressly incorporated by reference herein. Exemplary biologically active motifs are also described in more detail below. In additional aspects, the invention encompasses a macroscopic scaffold comprising a plurality self-assembling peptides wherein said peptides comprise a self-assembling domain comprising the sequence VEVK (SEQ ID NO: 1), wherein the peptide is capable of self-assembly. In certain aspects, the invention is directed to an aqueous composition comprising a plurality of peptides comprising a self-assembling motif, wherein each self-assembling motif comprises the amino acid sequence VEVK (SEQ ID NO:1) and wherein said peptides are capable of self-assembly. In another embodiment, the invention is a self-assembled nanostructure, wherein the nanostructure comprises a peptide comprising the sequence VEVK (SEQ ID NO:1) and wherein said peptides are capable of self-assembly. In yet another embodiment, the invention is a method of preparing a self-assembled nanostructure comprising forming an aqueous mixture of peptides comprising the sequence VEVK (SEQ ID NO:1), wherein said peptides are capable of self-assembly, under conditions suitable for self-assembly of the peptides. In a further embodiment, the invention is a macroscopic material comprising a plurality of peptides, wherein each peptide comprises the sequence VEVK (SEQ ID NO:1), wherein said peptides are capable of self-assembly. In some aspects, the material is composed of of β-sheets. In additional aspects, the invention is a method for in vitro cell culture comprising adding a macroscopic membrane of the invention to a cell culture medium comprising cells, thereby forming a membrane/culture mixture; and b) maintaining the mixture under conditions sufficient for cell growth. In yet another embodiment, the invention is a macroscopic scaffold comprising a plurality self-assembling peptides, wherein said peptides comprise a self-assembling motif comprising the amino acid sequence VEVK (SEQ ID NO:1) and wherein said peptides are capable of self-assembly wherein said peptides self-assemble into a β-sheet macroscopic scaffold; and wherein said macroscopic scaffold encapsulates living cells, said cells being present in said macroscopic scaffold in a three-dimensional arrangement. In certain embodiments, the peptide comprising the sequence VEVK (SEQ ID NO:1) is VEVKVEVKV (SEQ ID NO: 2) or VEVKVEVKVEVK (SEQ ID NO: 3). In certain additional aspects, the peptides comprising the sequence VEVK (SEQ ID NO: 1) comprises:
  a. A first amino acid domain that mediates self-assembly, wherein the first amino acid domain comprises the sequence VEVK (SEQ ID NO:1) and wherein the peptide is capable of self-assembly in isolated form; and
  b. A second amino acid domain that does not mediate self-assembly in isolated form, wherein the second amino acid domain comprises a biologically active motif.

Biologically active motifs

It has been previously described (for example, in U.S. Patent Application Publication No. 2009/0162437) that it is possible to modify peptide capable of self-assembly such as those described above by incorporating an additional domain that does not self-assemble, without eliminating the ability of the modified peptides to self-assemble to form a macroscopic structure. Therefore, in one embodiment, the self-assembling peptide comprises (a) a first amino acid domain that mediates self-assembly, wherein the domain comprises alternating hydrophobic and hydrophilic amino acids that are complementary and structurally compatible and wherein said domain self-assembles into a macroscopic structure when present in unmodified form; and (b) a second amino acid domain that does not self-assemble in isolated form. Such self-assembling peptides have been described, for example, in U.S. Pat. Application Publication Nos. 2005/0181973 and 2009/0162437A1, the contents of which are herein incorporated by reference.

In some embodiments of the invention, the second amino acid domain is a biologically active peptide motif Biologically active motifs that can be used according to the present invention include those described in U.S. Pat. App. Pub. No. 2005/0181973 and in Gelain et al. (2006). PLoS ONE 1(1): e119. doi:10.1371/journal.pone.0000119, the contents of which are incorporated by reference herein. Biologically active motifs include, for example, short peptide sequences from proteins in the cellular basement membrane that have been identified as participating in several biological functions such as cell attachment, proliferation, differentiation and migration (Iwamoto et al. (1987). Science 238: 1132-34; Kleinman et al. (1989), PNAS 87: 2279-83; Koliakos et al. ((1989), J. Biol. Chem. 264, 2313-2323). Various biologically active motifs have been identified, for example, in laminin, collagen IV, nidogen, proteoglycans and vascular endothelial cells. For example, the biologically active motif can be an RGD peptide, such as a repetitive RGD sequence such as PRGDSGYRGDS (SEQ ID NO:15). Another example of a biologically active motif is the sequence AASIKVAVSADR (SEQ ID NO: 49) derived from the laminin α chain promoted activity of neurite extension by PC12 cells, the peptide CSRARKQAASIKVAVSADR (SEQ ID NO: 50) induced degradation of Matrigel matrix by human umbilical vein endothelial cells (HIVEC). In addition, the sequences YIGSR (SEQ ID NO: 5), PDSGR (SEQ ID NO: 4) and RYVVLPR (SEQ ID NO: 9) located on the β1 chain of laminin promoted cell adhesion. The sequence KAFDITYVRLKF (SEQ ID NO: 51) from the laminin γ1 chain also promoted HUVEC adhesion and tube formation, as well as neuronal cell adhesion and neurite outgrowth. The peptide sequence TAGSCLRKFSTM (SEQ ID NO: 52) from type IV collagen was found to specifically bind to heparin. Additionally, RGD sequences, found, for example, in nidogen, serve as cell attachment site.

Non-limiting examples of biologically active motifs that can be used according to the invention are shown in Table 2 below.

TABLE 2

| SEQ ID NO | Peptide sequence | Protein |
|---|---|---|
| 49 | AASIKVAVSADR | Laminin-1 |
| 50 | CSRARKQAASIKVAVSADR | Laminin-1 |
| 5 | YIGSR | Laminin-1 B1 chain (amino acids 950-954) |
| 4 | PDSGR | Laminin-1 B1 chain (amino acids 923-927) |
| 9 | RYVVLPR | Laminin-1 B1 chain (amino acids 662-668) |
| 51 | KAFDITYVRLKF | Laminin-1 |
| 52 | TAGSCLRKFSTM | Collagen IV |
| 8 | RNIAEIIKDI | Laminin-1 |
| 53 | YVRL | Laminin-1 |
| 54 | IRVTLN | Laminin-1 |
| 55 | TTVKYIFR | Laminin-1 |
| 56 | SIKIRGTY | Laminin-1 |
| 57 | RQVFQVAYIIIKA | Laminin-1 |
| 58 | FQIAYVIVKA | Laminin-1 |
| 59 | GQLFHVAYIIIKA | Laminin-1 |
| 60 | FHVAYVLIKA | Laminin-1 |
| 61 | LENGEIVSLVNGR | Laminin-1 |
| 10 | LGTIPG | Laminin-1 B1 chain (amino acids 463-468) |
| 62 | DGEA | fibronectin |
| 63 | REDV | fibronectin |
| 64 | GVGVP | Elastin |
| 65 | GVGVAP | Elastin |

TABLE 2-continued

| SEQ ID NO | Peptide sequence | Protein |
|---|---|---|
| 6 | IKVAV | Laminin A chain (amino acids 2116-2120) |
| 66 | PFSSTKT | Bone marrow homing peptide 2 |
| 67 | SKPPGTSS | Bone marrow homing peptide 1 |
| 68 | SDPGYIGSR | Laminin |
| 8 | RNIAELLKDI | Laminin-1 B2 chain (amino acids 1577-1586) |
| 69 | PRGDSGYRGDSG | Collagen IV |
| 15 | PRGDSGYRGD | RGD motif |
| 70 | GFLGFPT | myelopeptide |
| 71 | YGPDSGR | RGD motif |
| 14 | YRGDS | RGD motif |
| 13 | PDSGR | RGD motif |
| 7 | LRE | Laminin-1 S chain (amino acids 1705-1707) |
| 11 | PVGLIG | MMP degradable motif |
| 12 | GPVGLIG | MMP degradable motif |

In some embodiments, the biologically active motif is an amino acid motif that participates in tissue regeneration. In yet another embodiment, the biologically active motif is an amino acid motif that participates in periodontal tissue regeneration. Non-limiting examples of biologically active motifs that participate in periodontal tissue regeneration include, but are not limited to, laminin cell adhesion motifs, an RGD peptide and matrix metalloproteinase degradable motifs.

Laminin is the main component of the basement membrane which is both a structural component supporting cells and provides cells with an instructive microenvironment that modulates their functions. It has been reported that laminin has specific cell adhesion properties, to which periodontal ligament fibroblasts and/or osteoblasts can adhere to (Palaiologou et al. (2001), J. Periodontol. 72: 798-807; Giannopoulou et al. (1996), J Dent Res 75: 895-902; Grzesik et al. (1998), J. Dent. Res. 77: 1606-1612). Non-limiting examples of laminin cell adhesion motifs are IKVAV (SEQ ID NO:6), LGTIPG (SEQ ID NO:10), RYVVLPR (SEQ ID NO:9), PDSGR (SEQ ID NO:4), YIGSR (SEQ ID NO:5), LRE (SEQ ID NO: 7) and RNIAEIIKDI (SEQ ID NO: 8).

An RGD peptide is a peptide that comprises contains an RGD (Arg-Gly-Asp) amino acid sequence. RGD is the key binding or recognition sequence for integrins, cell surface receptors that mediate adhesion between cells and the extracellular matrix (ECM). RGD peptides have been reviewed, for example, in Ruoslahti et al. (1996), Annual Review of Cell and Development Biology, 12: 697-715 and D'Souza et al., Trends in Biochemical Sciences 16: 246-50, the contents of each of which are expressly incorporated by reference herein. PRGDS (SEQ ID NO:13) and YRGDS (SEQ ID NO:14) are the most commonly occurring RGD motifs in natural proteins. An additional exemplary RGD sequence is PRGDSGYRGD (SEQ ID NO: 15), GRGDSP (SEQ ID NO:

83). By repetition of the RGD binding sequence, the possibility of attachment to the cell is increased. Binding is additionally affected by structural conformations because repetition increases the likelihood of effective conformation (Kantlehner et al. (2000)). A repetitive RGD sequence is a peptide sequence that includes at least two RGD sequences; for example, PRGDSGYRGD (SEQ ID NO:15) includes two RGD sequences.

Matrix metalloproteinases (MMPs) belong to a family of proteases that degrade extracellular matrix components and play an important role in tissue regeneration. These proteins make way for cells to expand, allow the extracellular matrix to be remodeled and release embedded growth factors and other signals from the extracellular matrix to stimulate cell differentiation and tissue growth. Incorporating MMP-cleavable substrate into self-assembling peptide scaffolds is an attractive strategy to engineer a dynamic mechanism for eliciting cell and tissue remodeling activities (Turk et al. (2001), Nat. Biotechnol. 19: 661-7). An exemplary MMP degradable motif is PVLIG (SEQ ID NO:11).

In certain embodiments of the invention, the addition of the non self-assembling amino acid domain does not prevent the modified peptide from self-assembling, e.g., to form nanofibers, a macroscopic structure, or both. In certain additional aspects, the modified peptide self-assembles to form a macroscopic structure composed of nanofibers. It is to be understood that an unmodified self-assembling peptide can be altered in any of a number of ways described above that does not include addition of amino acids to the peptide and these alterations are referred to herein as alteration and/or derivitazation. The modified self-assembling peptides of the invention are distinct from naturally occurring molecules, for example, they are not found in naturally occurring molecules, although one or more of the amino acid domains in an inventive peptide may occur in a naturally occurring molecule. They can therefore be considered "isolated" or "synthetic", meaning that the total sequence of the peptide does not occur in nature without the intervention of man.

It is additionally to be understood that the biologically active motif can be placed (e.g., attached via a linking group) closer to the N-terminal end or to the C-terminal end of the first domain comprising a peptide that self-assembles in isolated form. Biologically active motifs, which can be the same or can be different, can additionally be placed at both the N-terminal and C-terminal ends of the first domain.

In certain embodiments of the invention, the conditions under which self-assembly of the modified self-assembling peptide occurs are the same as the conditions under which the corresponding unmodified self-assembling peptide assembles. In other embodiments of the invention, the conditions under which self-assembly of the modified self-assembling peptide occurs are different from the conditions under which the corresponding unmodified self-assembling peptide assembles. In this case, the conditions for self-assembly of the modified self-assembling peptide are the same as the conditions under which a different (non-corresponding) unmodified self-assembling peptide self-assembles.

In certain aspects, the second amino acid domain permits assembly of the first amino acid domain so that the peptide assembles to form nanofibers, and/or a macroscopic structure. In preferred embodiments of the invention the peptide forms beta-sheets. In certain embodiments of the invention, an amino acid domain is at least 3 amino acids; at least 4 amino acids, at least 5 amino acids, at least 6 amino acids, at least 7 amino acids, at least 8 amino acids, at least 9 amino acids, at least 10 amino acids, or more, e.g., 15 or 16 amino acids, 20 amino acids, etc. However, it will generally be desirable to limit the length of the second amino acid domain so as not to interfere too greatly with self-assembly. For example it may be preferable to limit the length of the second amino acid domain to 20 amino acids or less, 16 amino acids or less, 12 amino acids or less, 10 amino acids or less, 8 amino acids or less, etc. It may be desirable to maintain a certain ratio of amino acids in the self-assembling and non self-assembling portions of the peptide. For example, in certain embodiments of the invention it may be desirable for the non self-assembling domain to constitute 50% of less of the total number of amino acids in the peptide.

It is possible that, under some circumstances, including a non self-assembling domain between self-assembling portions rather than at an N or C terminus will be more likely to disrupt self-assembly, since the non self-assembling portion cannot freely extend from a self-assembled structure in such a case. Furthermore, if contained between two self-assembling portions, there is likely to be less opportunity for the motif to interact freely with cells and/or molecules such as proteins present in the culture environment. Thus for various reasons it may be preferable to add the non self-assembling portion to the N or C terminus rather than to insert it between two self-assembling portions.

In addition to amino acid domains which sequences are derived from naturally occurring proteins such as those mentioned above, amino acid domains from growth factors, cytokines, chemokines, peptide hormones, peptide neurotransmitters, other biologically active peptides found in the body and the like can also be used (See, for example, Goodman and Gilman, The Pharmacological Basis of Therapeutics, 10th Ed. McGraw Hill, 2001 and Kandel et al., Principles of Neural Science, 4th ed., McGraw Hill, 2000).

Other biologically active motifs can be identified according to a number of criteria including, but not limited to, those described by Yamada (1991), J. Biol. Chem, 266: 12809-12812. While Yamada describes tests for biological relevance for the case of adhesive recognition sequences, the criteria given may be applied more widely. A putative active peptide motif can be identified as biologically active when a synthetic peptide containing the sequence displays activity after conjugation to a carrier (e.g., IgG, albumin, beads), even if inactive when adsorbed directly on a substrate such as glass, plastic, etc., though they may also display activity when conjugated to a substrate. A soluble form of a biologically active peptide motif can competitively inhibit the function of an intact protein in which the motif is naturally found. Alteration of the peptide sequence can eliminate the function of the peptide. A biologically active peptide can bind to the same cellular receptor or naturally occurring biomolecule as a naturally occurring protein containing the peptide. A range of different peptide concentrations can be tested, and various combinations can be used.

The two or more amino acid domains can be joined using methods known to those of ordinary skill in the art. Non-limiting examples include the use of a linker or bridge, which may be one or more amino acids or a different molecular entity. A linker domain consisting of one or more glycine (G) residues, e.g., 1, 2, 3, 4, 5, etc. glycines, can be used. The use of glyicine in the linker domain is advantageous because this amino acid is small and has a nonpolar side chain, thus minimizing the likelihood of substantial interference with self-assembly. Other exemplary amino acids are alanine or other amino acids having nonpolar side chains can also be used.

While the modified peptides described in the examples were made by solid phase synthesis of the extended peptide, resulting in a linear chain, variations in which the modifying motif is conjugated or cross-linked to a side chain are also encompassed within the present invention. Methods for achieving such conjugation or cross-linking are well known in the art. For example, a peptide containing a cysteine residue (or any amino acid modified to include a sulfur atom) can be coupled to a second peptide containing a sulfur atom by formation of disulfide bonds. Thus, in general, the modified self-assembling peptide may be a single linear polymer of amino acids joined by peptide bonds (a structure that may be preferred), or may have a branched structure in which two polymers of amino acids (each being a polymer of amino acids joined by peptide bonds) are attached to one another either covalently or non-covalently (e.g., via a biotin-avidin interaction). Non-limiting examples of cross-linking methods include, but are not limited to, the glutaraldehyde method which couples primarily through the V-amino group and W-amino group, maleimide-sulfhydryl coupling chemistries (e.g., the maleimidobenzoyl-N-hydroxysuccinimide ester (MBS) method), and periodate oxidation methods. In addition, numerous cross-linking agents are known. Exemplary cross-linking agents include, e.g., carboiimides, N-Hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), etc. For additional information on conjugation methods and crosslinkers see generally the journal Bioconjugate Chemistry, published by the American Chemical Society, Columbus Ohio, P.O. Box 3337, Columbus, Ohio, 43210. See also "Cross-Linking", Pierce Chemical Technical Library, available at the Web site having URL www.piercenet.com and originally published in the 1994-95 Pierce Catalog and references cited therein and Wong SS, Chemistry of Protein Conjugation and Crosslinking, CRC Press Publishers, Boca Raton, 1991. Bifunctional crosslinking reagents contain two reactive groups, thereby providing a means of covalently linking two target groups. The reactive groups in a chemical crosslinking reagent typically belong to the classes of functional groups including succinimidyl esters, maleimides, and iodoacetamides. A number of common schemes for forming a heteroconjugate involve the indirect coupling of an amine group on one biomolecule to a thiol group on a second biomolecule, usually by a two- or three step reaction sequence. The high reactivity of thiols and their relative rarity in most biomolecules make thiol groups good targets for controlled chemical crosslinking. If neither molecule contains a thiol group, then one or more can be introduced using one of several thiolation methods. The thiol-containing biomolecule may then be reacted with an amine-containing biomolecule using a heterobifunctional crosslinking reagent, e.g., a reagent containing both a succinimidyl ester and either a maleimide or an iodoacetamide. Amine-carboxylic acid and thiol-carboxylic acid crosslinking may also be used. For example, 1-Ethyl-3-(3-dimethylaminopropyl) carbodiimide (EDAC) can react with biomolecules to form "zero-length" crosslinks, usually within a molecule or between subunits of a protein complex. In this chemistry, the crosslinking reagent is not incorporated into the final product.

Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or tris-(2-cyanoethyl)phosphine. Amines can be indirectly thiolated by reaction with succinimidyl 3-(2-pyridyldithio)propionate (SPDP) followed by reduction of the 3-(2-pyridyldithio) propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Tryptophan residues in thiol-free proteins can be oxidized to mercaptotryptophan residues, which can then be modified by iodoacetamides or maleimides.

Self-assembly and methods for the use of self-assembling peptides

As described above, self-assembling peptides (including both modified and unmodified self-assembling peptides) self-assemble to form macroscopic structures under a variety of conditions, for example, upon the addition of monovalent cations to an aqueous peptide solution or upon the introduction of a peptide solution to a solution containing monovalent cations. Prior to self-assembly, the peptides can be dissolved in a solution that is substantially free of monovalent ions (e.g., cations) or contains only a low concentration of such ions, e.g., less than 10, 5, 1, 0.5, or 0.1 mM. Self-assembly may be initiated or substantially accelerated by the addition of an ionic solute to a peptide solution or by a change in pH. For example, NaCl at a concentration of between 5 mM and 5 M induces the assembly of the peptides to form macroscopic structures within a few minutes. Lower concentrations of NaCl can also induce assembly but at a slower rate. Certain of the peptides can also self-assemble in the absence of significant concentrations of ions, in a process that may be dependent on pH. For example, certain of the peptides may remain in solution at a pH of approximately 3.0 but may self-assemble when the pH is raised. Alternatively, self-assembly can be initiated by introducing the peptides into a solution comprising ions, e.g., standard phosphate buffered saline (PBS), tissue culture medium, or a physiological fluid such as blood, cerebrospinal fluid (CSF), etc. The peptides can thus self-assemble at a location in vivo. Preferred ions include monovalent cations such as Li+, Na+, K+, and Cs+. Preferably, the concentration of the ion is at least 5, 10, 20, or 50 mM in order to induce or substantially accelerate self-assembly. One of ordinary skill in the art will be able to select preferred concentrations of ions based on the particular peptide sequence and/or concentration and desired speed of assembly. In general, the strength of the resulting structure is increased in the presence of ions relative to the strength in the absence of ions, or at a lower ionic concentration (although it is noted that a plateau may be reached at which an increase in ion concentration does not result in increased strength).

In one embodiment, the invention is a nanostructure comprising a plurality of self-assembling peptides of the invention. Exemplary nanostructures include nanofilaments, nanofibers and nanoscaffolds. In another embodiment, the invention is a macroscopic structure comprising a plurality of self-assembling peptides described herein. In one embodiment, the macroscopic structure comprises homogenous self-assembling peptides. In another embodiment, the macroscopic structure comprises heterogenous self-assembling peptides. The term "homogenous self-assembling peptides" refers to a plurality of identical or same self-assembling peptides. The term "heterogenous self-assembling peptides" refers to a plurality of different self-assembling peptides. It is to be understood that self-assembling peptides can be different when two or more peptides in the mixture are different. In some embodiments, the macroscopic structure is a macroscopic membrane. The macroscopic membranes comprise, for example, a plurality of interwoven nanofilaments which in turn comprise the inventive self-assembling peptides. The initial concentration of the peptide is a factor in the size and thickness of the membrane formed. In general, the higher the peptide concentration, the higher the extent of membrane formation. In a further embodiment, the macroscopic membrane takes the form of β-sheets. In one embodiment, the invention is a macroscopic scaffold comprising a plurality of self-assembling peptides described herein wherein the self-assembling peptides self-assemble into a β-sheet macroscopic scaffold.

The formation of a self-assembled structure can be observed with the naked eye after staining with Congo Red, a dye which preferentially stains β-sheet structures and is commonly used to visualize abnormal protein deposition in tissues. Additional structural details can be observed under magnification. Scanning electron microscopy (SEM) allows structural details of the nanostructures to be observed. The β-sheet secondary structures of the membranes can additionally be confirmed by circular dichroism (CD) spectroscopy (Zhang et al (1993), PNAS 90: 3334-8; Zhang et al (1995). Biomaterials 16:1385; Zhang & Rich 1997, PNAS 94, 23-28, Yokoi et al., 2005. PNAS 102, 8414).

In certain aspects, the invention encompasses methods of using the inventive self-assembling peptides and self-assembled structures thereof as cell culture supports, as self-assembled monolayers imprinted onto solid supports, for the repair and replacement of various tissues, as a scaffold to encapsulate living cells, as part of a controlled-release drug delivery system and for promoting hemostasis. In certain aspects, the self-assembling peptide comprises the sequence VEVK (SEQ ID NO: 1). Other uses of self-assembling peptides have been described, for example in, U.S. Pat. App. Pub. Nos. 2002/0072074; 2002/0160471; 2004/0087013; 2004/0242469; 2005/0287186 and 2007/0203062, the contents of each of which are incorporated by reference herein.

In addition, because the macroscopic structure, macroscopic membranes and nanostructures formed by self-assembly of the peptides described herein are stable in serum, resistant to proteolytic digestion and alkaline and acidic pH, and are non-cytotoxic, the materials, membranes and filaments are useful in biomaterial applications, such as medical products (e.g., sutures), artificial skin or internal linings, slow-diffusion drug delivery systems supports for in vitro cell growth or culture and supports for artificial tissue for in vivo use. The structures can additionally be used in numerous applications in which permeable and water insoluble material are appropriate, such as separation matrices (e.g., dialysis membranes, chromatographic columns). Due to their permeability, the macroscopic membranes described herein are useful as slow-diffusion drug delivery vehicles. Because the membranes are resistant to degradation by proteases and stomach acid (pH 1.5), drug delivery vehicles made of these membranes could be taken orally. The small pore size of the membranes also makes them useful as filters, for example, to remove virus and other microscopic contaminants. The pore size (interfilament distance) and diameter of the filaments in the membranes can be varied by varying the length and sequence of the peptides used to form the membranes.

The macroscopic membranes can also be modified to give them additional properties. For example, the membranes can be further strengthened by cross-linking the peptides after membrane formation by standard methods. Collagen can be combined with the peptides to produce membranes more suitable for use as artificial skin; the collagen may be stabilized from proteolytic digestion within the membrane. Furthermore, combining phospholipids with the peptides may produce vesicles.

The macroscopic structures can also be useful for culturing cells. The addition of growth factors, such as fibroblast growth factor, to the peptide macroscopic structure can further improve attachment, cell growth and neurite outgrowth. The porous macrostructure can also be useful for encapsulating cells. The pore size of the membrane can be large enough to allow the diffusion of cell products and nutrients. The cells are, generally, much larger than the pores and are, thus, contained. In another embodiment, the invention is a macroscopic scaffold comprising a plurality of self-assembling peptides of the invention, wherein the self-assembling peptides self-assemble into a β-sheet macroscopic scaffold and wherein said macroscopic scaffold encapsulates living cells and wherein said cells are present in said macroscopic scaffold in a three-dimensional arrangement. The macroscopic scaffold can be prepared by incubating the self-assembling peptides and living cells in an aqueous solution under conditions suitable for self-assembly. The invention, also encompasses a method of regenerating a tissue, the method comprising administering to a mammal a macroscopic scaffold comprising the inventive self-assembling peptides are self-assembled in a β-sheet macroscopic scaffold, wherein said macroscopic scaffold encapsulates living cells, said cells being present in said macroscopic scaffold in a three-dimensional arrangement. The encapsulated cells are present in the macroscopic scaffold in a three-dimensional arrangement. In some embodiments, the method is used to treat or prevent a cartilage defect, connective tissue defect, nervous tissue defect, epidermal lining defect, endothelial lining defect, or arthritis. The macroscopic scaffold can be administered orally, percutaneously, intramuscularly, intravenously, subcutaneously, or by any other appropriate mode. In another embodiment, the invention is a method for in vitro cell culture comprising: (a) adding a macroscopic membrane which is formed by self-assembly of the inventive self-assembling peptides in an aqueous solution to a cell culture medium comprising cells, thereby forming a membrane/culture mixture; and (b) maintaining the mixture under conditions sufficient for cell growth.

The macroscopic membranes can also be used as a model system for investigating the properties of biological proteins structures with such unusual properties as extreme insolubility and resistance to proteolytic digestion including, but not limited to aggregates of β-amyloid protein and aggregated scrapie protein. The invention also encompasses method for the regeneration of nerves with the structures comprising self assembling peptides. For example, nerve regeneration can be promoted and directed by transplanting the self-assembled nanostructures along the correct path to their targets.

Peptide hydrogels described herein (for example, modified self-assembling peptides and/or unmodified self-assembling peptides comprising the sequence VEVK (SEQ ID NO:1)) can be used in culturing cells and tissues. Such methods are described in detail in U.S. Patent Application Publication No. 2009/0162437A1. In one embodiment, cells and tissues can be cultured on the surface of a hydrogel structure. In another embodiment, cells can also be encapsulated within the hydrogel. To encapsulate cells within a peptide structure, peptides and living cells can be incubated in an aqueous solution having an iso-osmotic solute at an appropriate concentration to support cell viability, under conditions that in which the peptides are not substantially self-assembled. In certain embodiments of the invention the solution contains a monovalent cation concentration of less than 10, 5, 1, or 0.1 mM or is substantially free of monovalent cations. The solution can also contain less than less than 10, 5, 1, or 0.1 mM or be substantially free of other ionic species, e.g., other cations or anions. Sufficient ion (e.g., monovalent cation) is added to the solution to initiate self-assembly of the peptides into a macroscopic structure, whereby the cells are encapsulated by the formation of the macroscopic structure. The encapsulated cells are present in the macroscopic structure in a three-dimensional arrangement. The solution can be contained in a pre-shaped mold dimensioned to establish a desired volume or shape of the macroscopic structure. Self-assembly can also be effected by a change in pH (e.g., a rise from a low pH to a higher pH).

Cells and agents such as bioactive molecules (e.g., differentiation-inducing agents, proliferation agents), therapeutic compounds, can also be introduced into the peptide solution prior to self-assembly. The self-assembly process then forms a structure that encapsulates the cells or molecules. To achieve even distribution of the cells or molecules within the structure it can be desirable to thoroughly mix the solution prior to initiation of self-assembly. It can be desirable to maintain the cells or agents in a solution that contains substantially no ions or only low concentration of ions in order to avoid initiation or acceleration of self-assembly immediately upon combining the cells or agents with the peptide solution. In this case the cells are preferably maintained in an iso-osmotic solute such as sucrose prior to combination with the peptide solution. The peptides themselves can be dissolved in an isoosmotic solution to which cells (e.g., a cell pellet) or agents are added. The resulting composition may be mixed to achieve a more uniform distribution of cells and/or agents, following which the composition is exposed to ions (e.g., ions are added to the composition, or the composition is mixed with a solution containing ions).

Cells can be cultured on the surface of a peptide hydrogel structure in a similar manner to that in which they are cultured on a conventional substrate such as a tissue culture dish or slide, or a tissue culture dish or slide that is coated with a biologically derived material such as collagen, Matrigel, etc. In general, cells can be cultured at any desired degree of confluence. If encapsulated, the cells are preferably present in the macroscopic structure in a three-dimensional arrangement. Conditions for culturing should preferably be close to physiological conditions. For example, the pH of the culture medium should preferably be close to physiological pH, preferably between pH 6-8, for example about pH 7 to 7.8, in particular pH 7.4. Physiological temperatures range between about 30° C. to 40° C.

Cells can be cultured on or within the peptide structure for any appropriate time, depending upon the cell number and density desired, the proliferation rate of the cells, and the time required for the desired cellular reprogramming to occur. These parameters will vary depending upon the particular cells and purposes for which the invention is to be used. One of ordinary skill in the art will be able to vary these parameters and to observe the effects of doing so, in order to determine the optimal time for maintaining cells in culture on or within the structure. In certain embodiments of the invention the cell are cultured for approximately 3 days, 7 days, 14 days, 21 days, 28 days, 56 days, or 90 days.

In some aspects, at least 40, 50, 60, 70, 80, 90, or 95% of the cells (either cultured on a surface or encapsulated) are viable 1, 2, 4, 6, or more weeks after formation of the macroscopic scaffold. In another embodiment, at least 50%, at least 60%, at least 70%, at least 80% or 90% of the cells are viable one day or one week after formation of the macroscopic scaffold.

In general, any cell type can be cultured and/or encapsulated in accordance with the present invention including, but not limited to, vascular endothelial cells and precursors thereof, bone marrow cells, periosteal cells, perichondrial cells, fibroblasts, skeletal myoblasts or myocytes, neuronal cells, hippocampal cells, epidermal cells, non-vascular endothelial cells or smooth muscle cells, keratinocytes, basal cells, spinous cells, granular cells, embryonic stem cells, lung cells, immune system cells, ovarian cells, pancreatic cells, cervical cells, liver cells, foreskin cells or periodontal ligament fibroblast cells. The cells can comprise embryonic, fetal, or adult stem cells, e.g., stem cells that are able to or can be induced to differentiate into any of the preceding cell types. In certain aspects, the cells are periodontal ligament fibroblasts.

The self-assembling peptides described above can also be used, for wound healing, tissue regeneration, periodontal tissue regeneration and/or in increasing matrix metalloprotease production in a target tissue. Peptide hydrogel structures optionally comprising cells growing on the surface thereof or encapsulated within may be implanted into the body using any suitable method. Non-limiting methods include surgical procedures and/or by injection. Routes of administration, including, but not limited to, oral, percutaneous, intramuscular, intravenous, subcutaneous or parental routes may be utilized. A person having skill in the art will readily be able to select an appropriate delivery technique.

Several different types of devices can be employed to administer the self-assembling peptides to the site of injury or to the site of tissue damage or regeneration (in other words, the site in need of tissue regeneration). It will be appreciated that the delivery can be accomplished using a syringe or a catheter. In some aspects of the invention, the self-assembling peptides are administered using a syringe. In some embodiments, the peptides in solution are unassembled or minimally assembled (e.g., where the solution has not formed a gel) are administered to the patient and assembly occurs after administration. In additional aspects, the peptides have self-assembled in vitro and are introduced into the body as an assembled matrix. Such methods are described in detail in U.S. Patent Application Publication No. 2009/0162437. In certain additional embodiments, the invention is directed to a syringe having two compartments wherein the first compartment comprises a solution comprising a self-assembling peptide and a second compartment comprising a gelation fluid. A gelation fluid is a fluid that when combined with the peptide solution results in the formation of a hydrogel. Exemplary gelation fluid include, for example, fluids comprising monovalent cations as described in detail above.

In certain aspects, the invention is a method of regenerating a damaged tissue in a patient in need thereof comprising administering a self-assembling peptide described herein. As will be appreciated by the skilled artisan, several conditions can damage tissue such that regeneration of said tissue would be therapeutically useful. Such conditions include, but are not limited to, arthritides, various neurological conditions, neuroendocrine disorders, muscular degeneration, muculotendenous failure, age-related degeneration, trauma, necrosis, cardiac disorder and surgical resection. The damaged tissue can for example be skeletal tissue, bone, tendon, connective or dental tissues.

In some embodiments, the invention is a method of treating a periodontal disease and/or regenerating dental tissue. In certain embodiments, the dental tissue is periodontal ligament tissue. Exemplary periodontal diseases are periodontitis, gingivitis, periimplantitis and peri-implant mucositis. In periodontitis, gums recede from the teeth and form pockets that become infected. Bacterial toxins and the immune system fighting the infection actually begin damaging the bone and connective tissue that hold teeth in place. Periimplantitis is a complication after surgical implantation of an alloplastic material into the jawbone and affects the tissues around an osseointegrated implant in function, resulting in loss of supporting bone. In certain embodiments, a therapeutically effective amount of a self-assembling peptide is administered to the periodontium. The periodontium and the tissues that make it up are illustrated in FIG. 1. The periodontium consists of four tissues, gingival, periodontal ligament, cementum and alveolar bone. The gingiva is a pink-colored keratinized mucus membrane that covers parts of the teeth and part of the alveolar bone. The periodontal ligament is a group of connective tissue fibers that attach the tooth to alveolar bone. The cementum is a calcified structure that covers the lower parts of the teeth. The alveolar bone is a set of ridges from the jaw bones (maxillary and mandible) in which the teeth are embedded. The area where periodontal disease is initiated is the gingival sulcus, a pocket between the teeth and the gums.

In additional aspects, the invention is a scaffold for periodontal tissue regeneration comprising a self-assembling peptide described herein. As used herein in the context of tissue regeneration and/or periodontal tissue regeneration, a scaffold is a degradable hydrogel. In certain additional aspects, the self-assembling peptide comprises a biologically active motif selected from the group consisting of a laminin cell adhesion motif, an RGD peptide and a matrix metalloprotease cleavable substrate. In a further embodiment, the self-assembling peptide comprises a lamin cell adhesion motif. The use of scaffolds in periodontal tissue engineering has been discussed, for example, in Ma et al. (2006) Scaffolding in tissue engineering. CRC Press Pp 438; Akman et al. (2010), J Biomed Mater Res 92(3): 953-62; Hollister (2005), Nature Mat. 4: 518-524, the contents of which are expressly incorporated by reference herein. Scaffolds are utilized, for example, to maintain tissue volume, as vehicles for delivering therapeutic and/or biologically active materials to the wound and for promoting selective colonization and proliferation. A goal in the treatment of periodontal disease is the generation of periodontal ligament. Conventional guided tissue regeneration for the treatment of periodontal disease mechanically blocks gingival tissue invasion (which has been shown to be associated with root resorption) while allowing the attachment of periodontal ligament fibroblasts [28a]. In some aspects of the invention, the scaffold for periodontal tissue regeneration biologically blocks gingival cell invasion and promotes periodontal ligament growth. For example, when the scaffold includes a laminin cell adhesion motif, periodontal ligament fibroblasts are able to adhere to the motif whereas gingival cells have less ability to adhere to the motif than periodontal ligament fibroblasts [27a-29a]. In one embodiment, the invention is a scaffold for tissue regeneration further comprising cells wherein the cells are periodontal ligament fibroblasts. In yet another aspect, the scaffold comprises a self-assembling peptide comprising a biologically active motif that periodontal ligament fibroblasts are capable of adhering to.

In an additional embodiment the invention is a method of treating periodontal disease comprising administering a scaffold described herein. The invention further encompasses a method of treating periodontal disease comprising administering a scaffold of the invention and further administering a solid biomaterial. In certain aspects, the solid biomaterial is osteoconductive. As will be appreciated by the skilled artisan, the solid biomaterial can be fabricated of any appropriate material including, but not limited to, calcium and/or phosphorous. Exemplary materials comprise calcium triphosphate and hydroxylapatite. An additional example of a biomaterial is made from β-tricalcium phosphate. Such a biomaterial is, for example, GEM 21 S® Growth-Factor Enhanced Matrix. The biomaterial can, for example, take the form of a powder, block forms and/or granules. In additional aspects, the solid biomaterial comprises pores having a diameter from about 100 to about 500 microns. The method of treating periodontal disease comprises administering a scaffold described herein and a solid biomaterial and further comprising administration of an additional bioactive agent, such as a pharmacologic agent (including, for example, small molecules and peptides). In some embodiments, the pharmacologic agent comprises a recombinant human protein and/or a growth factor. In a further embodiment, the growth factor is a human recombinant growth factor protein. Exemplary recombinant human proteins are recombinant human platelet-derived growth factor (rh-PDGF), recombinant human bone morphogenetic protein-7 (rh-BMP-7) and recombinant human basic fibroblast growth factor (rh-bFGF).

In an additional aspect, the invention is directed to a method of increasing extracellular matrix protein production in a tissue comprising administering a self-assembling peptide described herein. A preferred extracellular matrix protein is collagen.

The following Examples further illustrates the present invention but should not be construed as in any way limiting its scope.

EXEMPLIFICATION

Recently, several peptide molecules including RGD and laminin cell adhesion motifs have been reported to promote periodontal ligament fibroblasts activities [27a]-[29a]. RGD (Arg-Gly-Asp) is well known as a key binding sequence for cell attachment specifically working with integrin. Laminin is a main component of basement membrane. The basement membrane is not only important as a structural component supporting cells, but also gives to the cells an instructive microenvironment that modulates their function. Cell adhesion is a first phase of cell/material interaction and influences the cell's capacity to proliferate, migrate and differentiation. Therefore the fully-synthesis peptide scaffolds functionalized by RGD and laminin cell adhesion motifs show promise as a simple, safe and inexpensive material for periodontal therapy.

In the studies described below, we studied periodontal ligament fibroblasts activities on two designer self-assembling peptide scaffolds PRG and PDS in vitro. PRG is peptide scaffold RADA16 through direct coupling to a 2-unit RGD binding sequence PRGDSGYRGDS (SEQ ID NO: 15). PDS is RADA16 through direct coupling to a laminin cell adhesion motif PDSGR (SEQ ID NO: 4). And these scaffolds significantly promote periodontal ligament fibroblasts cell attachment, proliferation, migration and extracellular matrix protein production, especially type I and type III collagens, which are major extracellular matrix protein components of periodontal ligament [30a], [31a].

It is known that the formation of self-assembling peptide scaffold and its mechanical properties are influenced by several factors, one of which is the level of hydrophobicity

[11b-16b]. That is, in addition to the ionic complementary interactions, the extent of the hydrophobic residues, Ala, Val, Ile, Leu, Tyr, Phe, Trp (or single letter code, A, V, I, L, Y, F, W) can significantly influence the mechanical properties of the scaffolds and the speed of their self-assembly. Higher hydrophobicity corresponds to a shorter length of peptide required for self-assembly, easier scaffold formation, and better mechanical properties. However, this property does not necessarily promote cell migration, so additional active motifs may be needed to stimulate cell adhesion.

Adhesion between cells and the matrix is very important for cell growth. The functionalization of peptide scaffold with cell adhesion motifs RGD (Arg-Gly-Asp) and cell adhesion motifs from laminin has been shown to be effective in increasing cell proliferation, migration and differentiation [8b, 9b]. Recently, peptides that are sensitive to the enzymatic cleavage of matrix metalloproteinases (MMPs) have been added to synthetic polymers and peptide-amphiphiles[17-24]. MMPs belong to a family of proteases that degrade extracellular matrix components and therefore play important roles in tissue regeneration. They make space in the matrix for cells to expand and migrate, enabling extracellular matrix remodeling and tissue growth. In addition to cell adhesion motifs, incorporating MMP-cleavable substrates into self-assembling peptide scaffolds is an attractive strategy to engineer a dynamic mechanism for eliciting remodeling activities in cells and tissue.

Below is described the design of the two self-assembling peptides VEVK9 (Ac-VEVKVEVKV-CONH$_2$) (SEQ ID NO: 2), and VEVK12 (Ac-VEVKVEVKVEVK-CONH$_2$) (SEQ ID NO: 3) and the functionalization of VEVK9 by synthesizing extended sequences with a designed 2-unit RGD binding sequence (PRGDSGYRGDS (SEQ ID NO:15)) or one of two cell adhesion motifs derived from laminin (YIGSR (SEQ ID NO: 5), IKVAV (SEQ ID NO: 6)) added at the C-terminus. The designed 2-unit RGD sequence has previously been shown to be effective in osteoblasts and endothelial cell growth [8b, 25b]. The self-assembling peptide VEVK9 has only 9 amino acid residues and its functionalized peptides are shorter than those of RADA16-I, which has 16-amino acid residues, and VEVK9 has the potential for promoting cell activities in a similar way. We also report the functionalization of VEVK9 with an MMP-2 cleavable sequence. We inserted an MMP-2 cleavable sequence (PVGLIG ((SEQ ID NO: 19)) into the self-assembling peptide VEVK9. This sequence was selected by screening a combinatorial peptide library for optimal MMP substrates [26b]. The self-assembling peptide scaffold functionalized with this sequence, (RADA)$_3$PVGLIG (RADA)$_3$ (SEQ ID NO: 84), has been shown to be degradable by MMP-2, showing promise for use as a tissue engineering scaffold [19b].

In summary, we tested the potentiality of the functional motifs for periodontal tissue regeneration. We used human primary periodontal ligament fibroblasts (HPDLF) to compare the effects of these motifs on proliferation, migration and matrix protein production with non-functionalized self assembling peptide scaffolds, RADA16, VEVK9, VEVK12 as a control.

Example 1

Periodontal Ligament Fibroblasts Attachment, Migration and Matrix Protein Production on Peptide Scaffolds Methods
Peptide Scaffold;
1% RADA16 solution was obtained as PuraMatrix (3DM Inc./BD Bioscience). VEVK9, VEVK12 and the functionalized peptides were obtained from CPC Scientific (San Jose, Calif.) and dissolved in water at final concentration of 1% (v/w). The functionalized peptide solutions were then mixed with 1% RADA16, VEVK9 or VEVK12 solution at a ratio of 1:1. Each peptide solution was then loaded in the cell culture plate insert (BD Bioscience, Bedford, Mass.). The medium described below was added to induce hydrogel formation.

TABLE 3

Functionalized peptides

| Peptide | SEQ ID NO: | Sequence | Description |
|---|---|---|---|
| A | 18 | Ac(RADA)$_4$CONH$_2$ | Self assembling motif |
| B | 72 | Ac(RADA)$_4$GGPRGDSGYRGDSCONH$_2$ | Repetive RGD binding sequence |
| C | 73 | Ac(RADA)$_4$GGPDSGRCONH$_2$ | Laminin cell adhesion motif PDSGR |
| D | 74 | Ac(RADA)$_4$GGSDPGYIGSRCONH$_2$ | Laminin cell adhesion motif YIGSR |
| E | 75 | Ac-VEVKVEVKVCONH$_2$ | Self assembling motif |
| F | 76 | Ac-VEVKVEVKVEVKCONH$_2$ | Self assembling motif |
| G | 77 | Ac-VEVKVEVKVGPRGDSGYRGDSGCONH$_2$ | Repetive RGD binding sequence |
| H | 78 | Ac-VEVKVEVKVGPDSGRCONH$_2$ | Laminin cell adhesion motif PDSGR |
| I | 79 | Ac-VEVKVEVKVGYIGSRCONH$_2$ | Laminin cell adhesion motif YIGSR |
| J | 80 | Ac-VEVKVEVKVGGRNIAEIIKDICONH$_2$ | Laminin cell adhesion motif RNIAEIIKDI |
| K | 81 | Ac-VEVKVEVKVGIKVAVCONH$_2$ | Laminin cell adhesion motif IKVAV |

TABLE 4

Tested peptide scaffolds

| Code | Contents |
|---|---|
| RADA16 | 1% peptide A solution |
| PRG | 1% peptide B solution and 1% peptide A solution mix by 1:1 |
| PDS | 1% peptide C solution and 1% peptide solution A mix by 1:1 |
| SDP | 1% peptide D solution and 1% peptide solution A mix by 1:1 |
| VEVK9 | 1% peptide E solution |
| VEVK12 | 1% peptide F solution |
| vPRG_9 | 1% peptide G solution and 1% peptide E solution mix by 1:1 |
| vPDS_9 | 1% peptide H solution and 1% peptide E solution mix by 1:1 |
| vYIG_9 | 1% peptide I solution and 1% peptide E solution mix by 1:1 |
| vRNI_9 | 1% peptide J solution and 1% peptide E solution mix by 1:1 |
| vIKV_9 | 1% peptide K solution and 1% peptide E solution mix by 1:1 |
| vPRG_12 | 1% peptide G solution and 1% peptide F solution mix by 1:1 |
| vPDS_12 | 1% peptide H solution and 1% peptide F solution mix by 1:1 |
| vYIG_12 | 1% peptide I solution and 1% peptide F solution mix by 1:1 |
| vRNI_12 | 1% peptide J solution and 1% peptide F solution mix by 1:1 |
| vIKV_12 | 1% peptide K solution and 1% peptide F solution mix by 1:1 |

Cell culture of periodontal ligament fibroblasts

Primary isolated human periodontal ligament fibroblasts were commercially obtained from Lonza Inc. (HPDLF, Walkersville, Md.) and routinely grown in the culture medium (SCGM, Walkersville, Md.) on regular cell culture flask. The cells were plated at 2×104 cells on the gel in the inserts. The culture medium was changed every three days. Additional growth factors were not used.

Fluorescence microscopy

Following the experiments, the cells on the gel were fixed with 4% paraformaldehyde for 15 min and permeabilized with 0.1% Triton X-100 for 5 min at room temperature. Fluorescent Rhodamin phalloidin and SYTOX® Green (Molecular Probes, Eugene, Oreg.) were used for labeling F-actin and nuclei, respectively. Images were taken using a fluorescence microscope (Axiovert 25, ZEISS) or laser confocal scanning microscope (Olympus FV300).

Fluorescent immunostaining for type I and type III collagens visualization.

After the cell fixation, the primary antibody for type I collagen (5% Anti-collagen type I, Millpore, Mass.) was added and incubated at 37° for 40 min, then washing six times with PBS with 1% BSA. The second antibody (0.5% Alexa fluor 488 goat anti-rabbit IgG, Invitrogen) was added and incubated at 37° for another 40 min, then washing as well. After that, the primary antibody for type III collagen (0.5% Anti-collagen type III, Millpore, Mass.) was added and incubated at 37° for 40 min, then washing. Finally, the second antibody (0.5% Alexa fluor 594 goat ant-mouse IgG, Invitrogen) was added and incubated at 37° for another 40 min. Nonspecific staining as a control was performed by omitting primary antibodies.

Results and discussion

Cell attachment and proliferation

Figure 2:
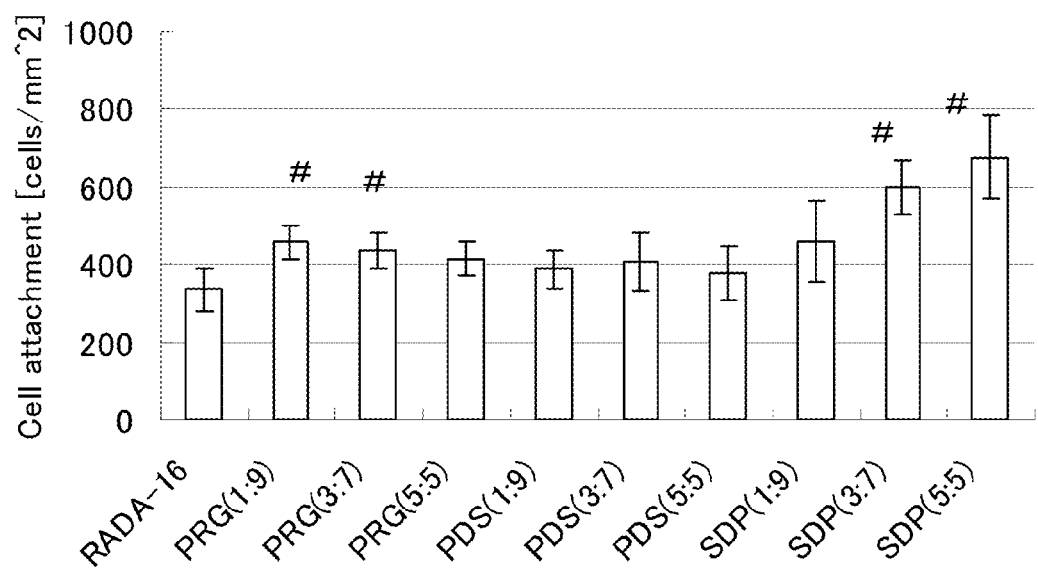
FIG. 2 is a bar graph showing cell numbers on each functionalized peptide scaffold after two weeks of cell culture and using different mix ratios (PRG(1:9) means mix ratio of PRG:RADA16=1:9. # indicates p<0.01 t-test); PRG and RADA16 are described in detail in the Examples section).
Figure 3A:
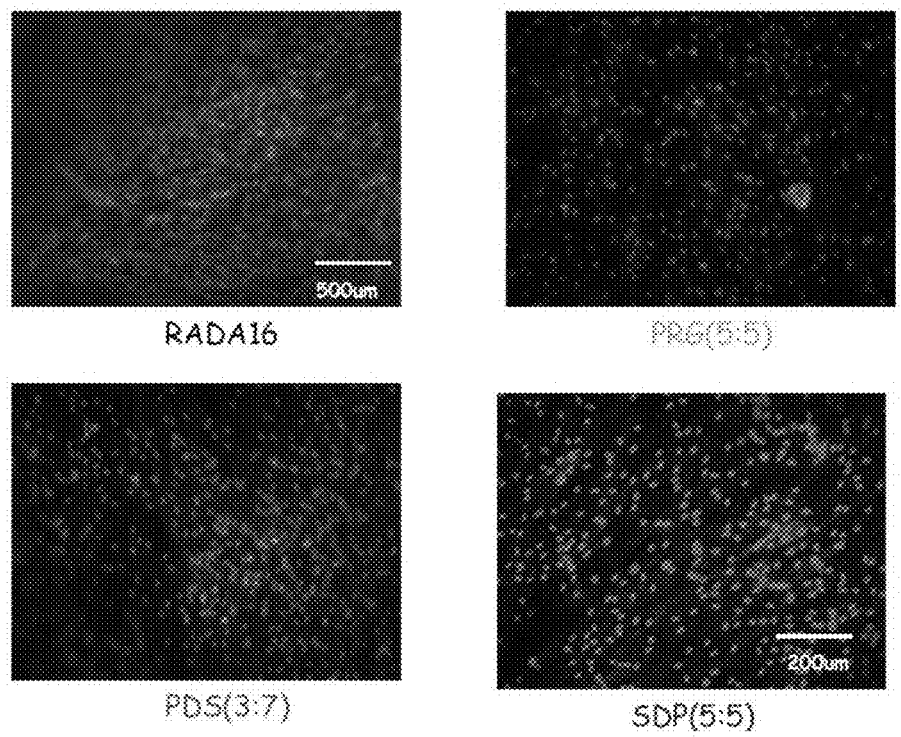
FIGS. 3A and 3B are photographs showing cell morphology on each functionalized peptide scaffold after two weeks cell culture.
Figure 3B:
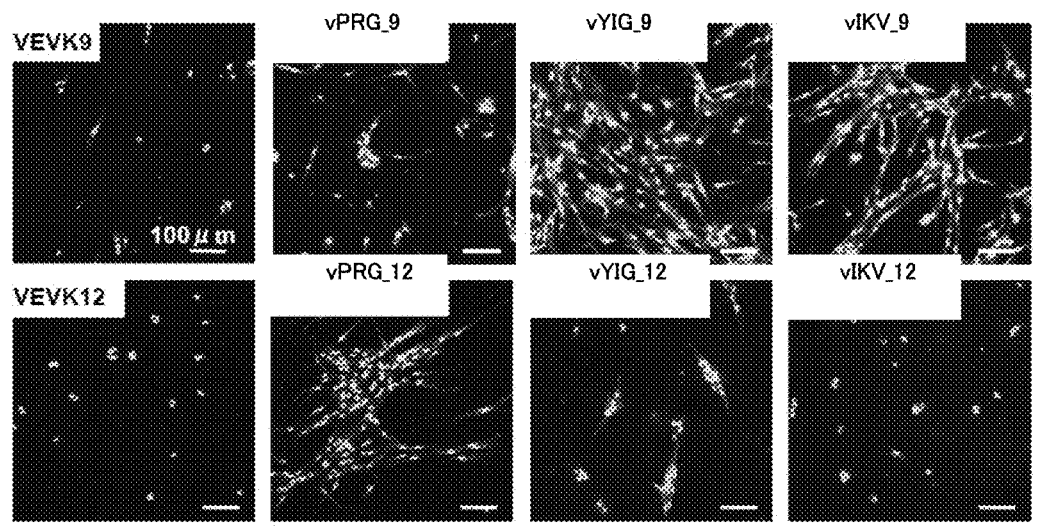

The functionalized peptide scaffolds promoted greater cell attachment and proliferation compared to RADA16, VEVK9 or VEVK12 (FIGS. 2, 3A and 3B). We also tested different mix ratios. PRG(1:9) means mix ratio of PRG: RADA16=1:9. # means p<0.01 t-test.

Cell migration into peptide scaffolds

Figure 4:
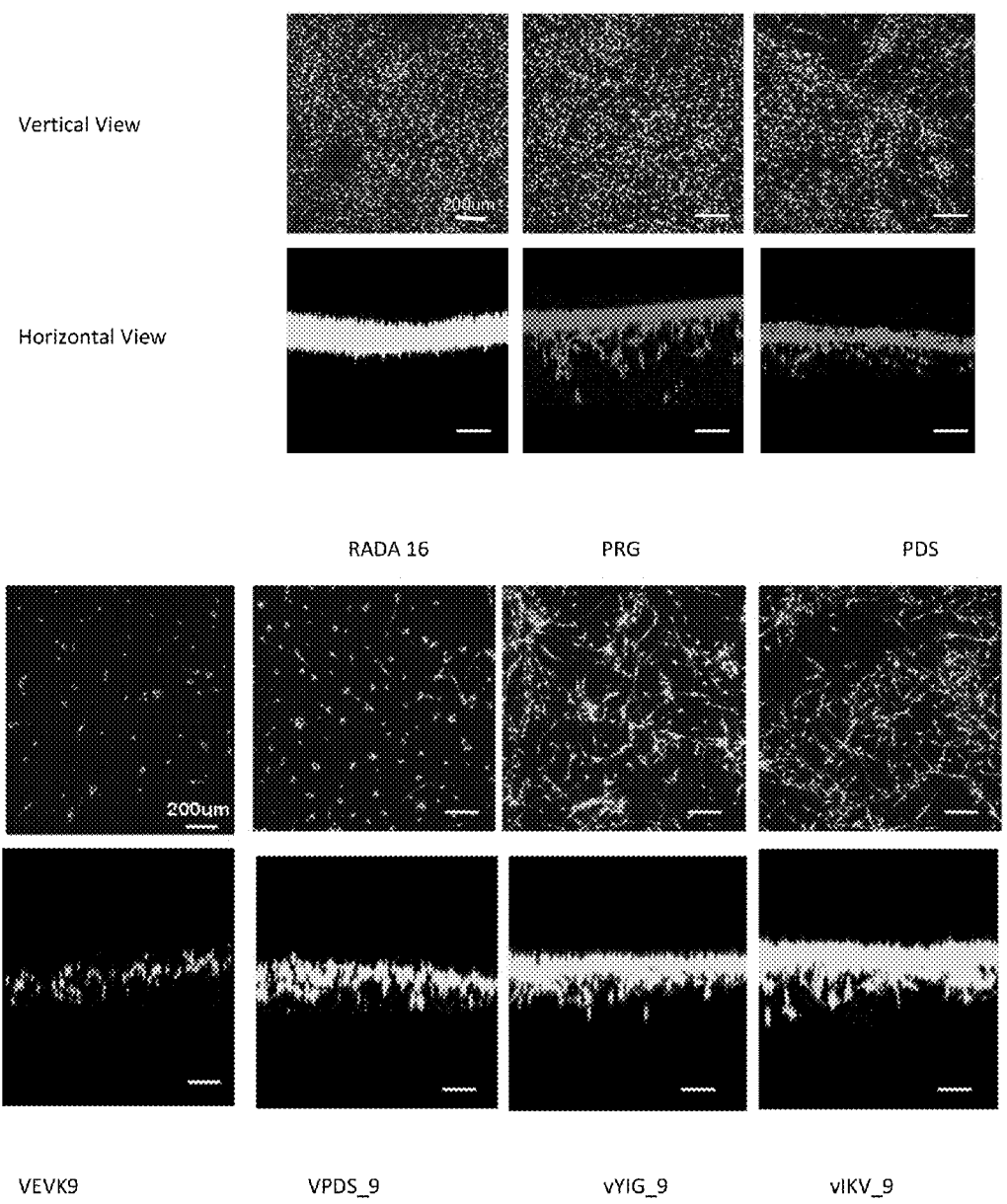
FIG. 4 shows confocal microscope images showing cell migration into peptide scaffolds after two weeks cell culture.

The functionalized peptide scaffolds PRG and PDS promoted greater cell migration into peptide scaffolds compared to RADA16 (FIG. 4).

Matrix proteins production

Figure 5:
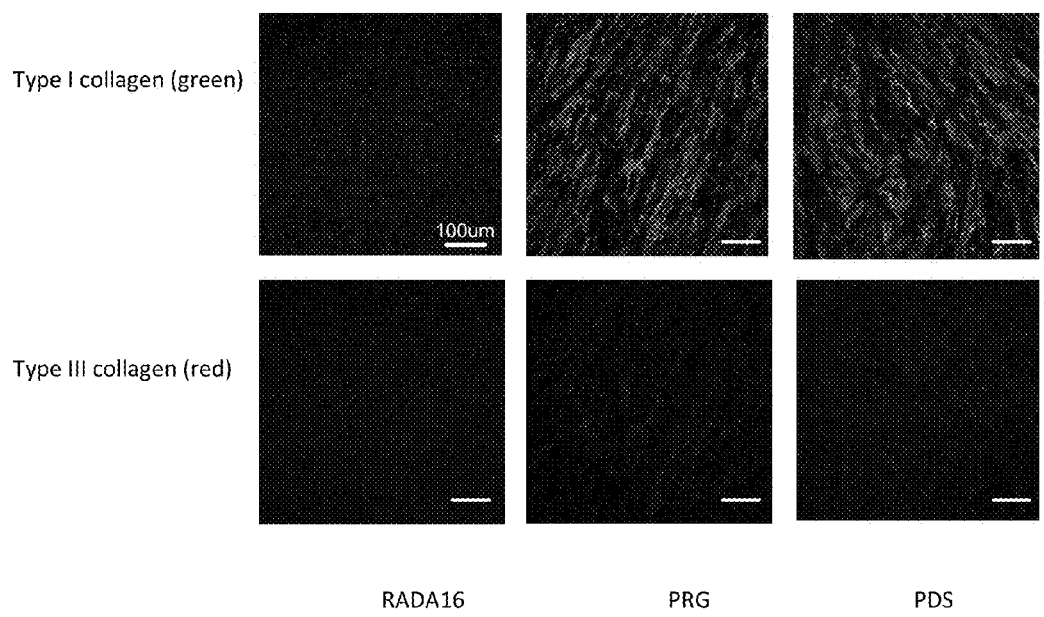
FIG. 5 are fluorescent immunostaining images type I (green) and type III (red) collagens production on peptide scaffolds after six weeks cell culture.

The functionalized peptide scaffolds PRG and PDS promoted greater type I and type III collagens compared to RADA16 (FIG. 5). Type I and type III collagens are well known as major matrix proteins of periodontal ligament.

Example 2

Selective Cell Reproduction of Peptide Scaffolds (Comparison Between Periodontal Ligament and Gingival Fibroblasts)

We tested the selective cell reproduction property of the functional scaffolds, using two periodontal cells, periodontal ligament fibroblasts and gingival fibroblasts.

Method

Cell culture of gingival fibroblasts

Human gingival fibroblasts were commercially obtained from ATCC (HGF-1) and routinely grown in the culture medium (DMEM+10% FBS) on regular cell culture flask. The cells were plated at 2×104 cells on the gel in the inserts. The culture medium was changed every three days.

Results and discussion

Figure 6:
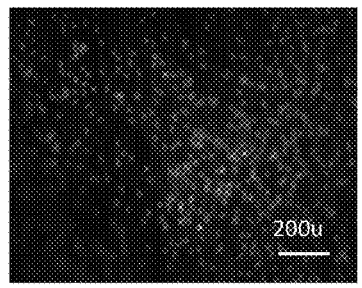
FIG. 6 shows a comparison study between periodontal ligament fibroblasts and gingival fibroblast on the peptide scaffold PDS (PDS is described in detail in the Examples section).
Figure 6:
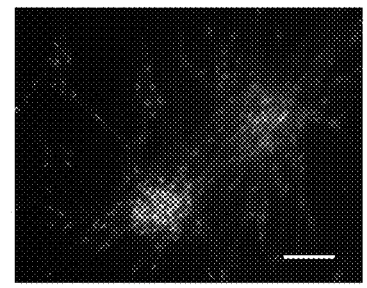
Figure 6:
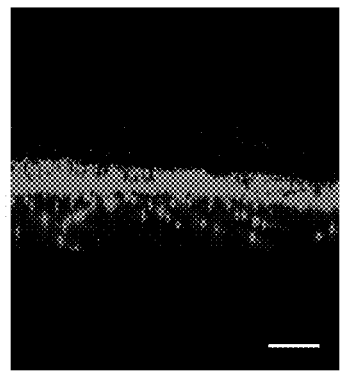
Figure 7:
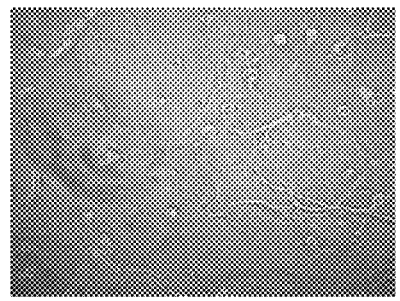
FIG. 7 shows a comparison study between periodontal ligament fibroblasts and gingival fibroblast on the peptide scaffolds vPDS_9, vYIG_9 and vIKV_9 (described in detail in the Examples section).
Figure 7:
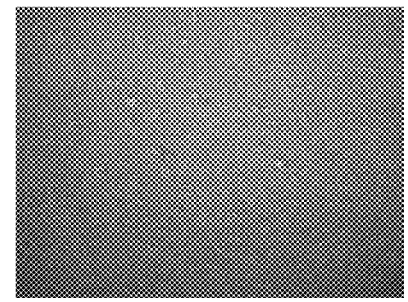
Figure 7:
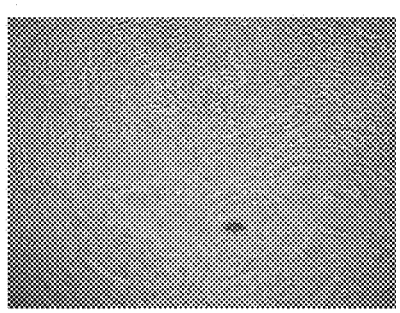
Figure 7:
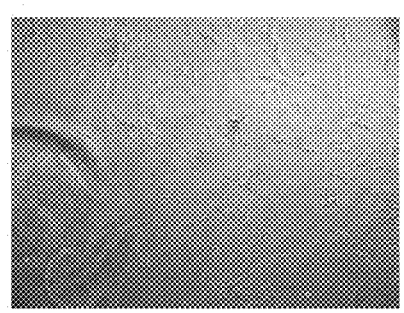
Figure 7:
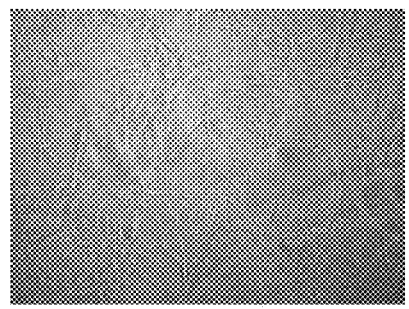

The functionalized peptide scaffold PDS showed selective cell attachment and migration (FIG. 6). Periodontal ligament fibroblasts spread on the surface of the scaffold and migrated into the scaffolds. In comparison, gingival fibroblasts didn't adhere to the scaffold well and migrate into the scaffold at all. The peptide scaffold RADA16 did not show migration in both fibroblasts (not shown). These results suggest that the scaffold may have good potential to provide space and favorable niche to grow periodontal ligament fibroblasts and reconstruct periodontal tissue, restricting the repopulation of the space by gingival fibroblasts. The functionalized peptide scaffolds vPDS_9, vYIG_9 and vIKV_9 also showed selective cell attachments (FIG. 7).

Example 3

Periodontal Ligament Fibroblast Migration into Peptide Scaffold Functionalized with MMP Degradable Motif We tested the potentiality of the peptide scaffold functionalized with MMP degradable motif through the effect of periodontal ligament fibroblasts migration.

Methods

Peptide Scaffold

The functionalized peptide was obtained from CPC Scientific (San Jose, Calif.) and dissolved in water at final concentration of 1% (v/w) as well. The functionalized peptide solutions were then mix with 1% VEVK9 or VEVK12 solution. The each peptide solution was loaded in the cell culture plate insert (BD Bioscience, Bedford, Mass.). The medium described below was added to induce hydrogel formation.

TABLE 5

Functionalized peptide

| Peptide | SEQ ID NO: | Sequence | Description |
|---------|------------|----------|-------------|
| L | 82 | Ac-VEVK GPVGLIG VEVK CONH$_2$ | MMP cleavage site GPVGLIG |

TABLE 6

Tested peptide scaffolds

| Code | Contents |
|------|----------|
| VEVK9 | 1% peptide E solution |
| VEVK12 | 1% peptide F solution |
| vPVG_vPRG_9 | 1% peptide L solution, 1% peptide G solution and 1% peptide E solution mix by 1:1:2 |
| vPVG_vYIG_9 | 1% peptide L solution, 1% Seq. 9 peptide solution and 1% peptide E solution mix by 1:1:2 |
| vPVG_vIKV_9 | 1% peptide L solution, 1% peptide I solution and 1% peptide E solution mix by 1:1:2 |
| vPVG_vPRG_12 | 1% peptide L solution, 1% peptide G solution and 1% peptide F solution mix by 1:1:2 |
| vPVG_vYIG_12 | 1% peptide L solution, 1% peptide I solution and 1% peptide F solution mix by 1:1:2 |
| vPVG_vIKV_12 | 1% peptide L solution, 1% peptide K solution and 1% peptide F solution mix by 1:1:2 |

Results

Figure 8:
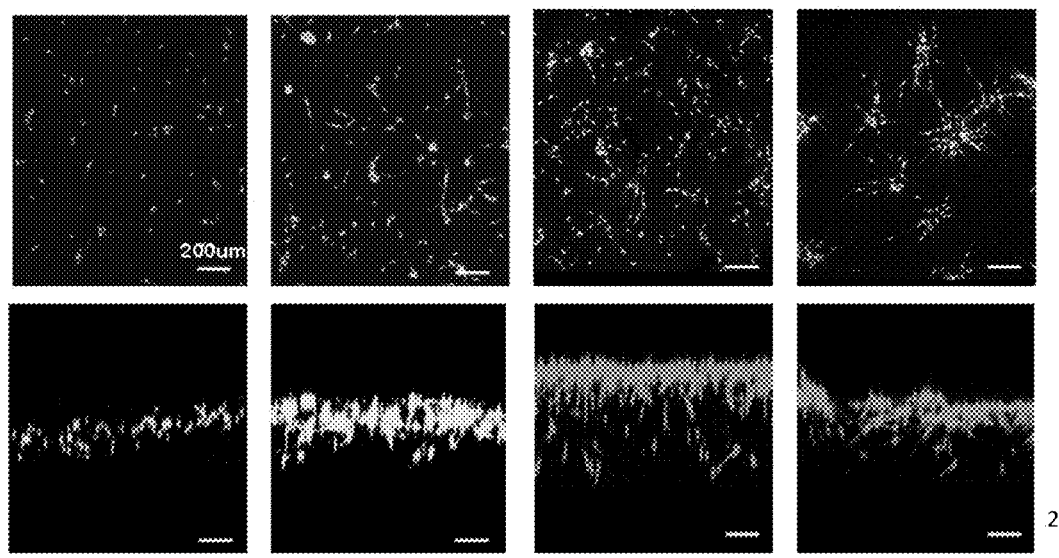
FIG. 8 is confocal microscope images showing that functionalized peptide vPVG promoted cell migration.
Figure 9:
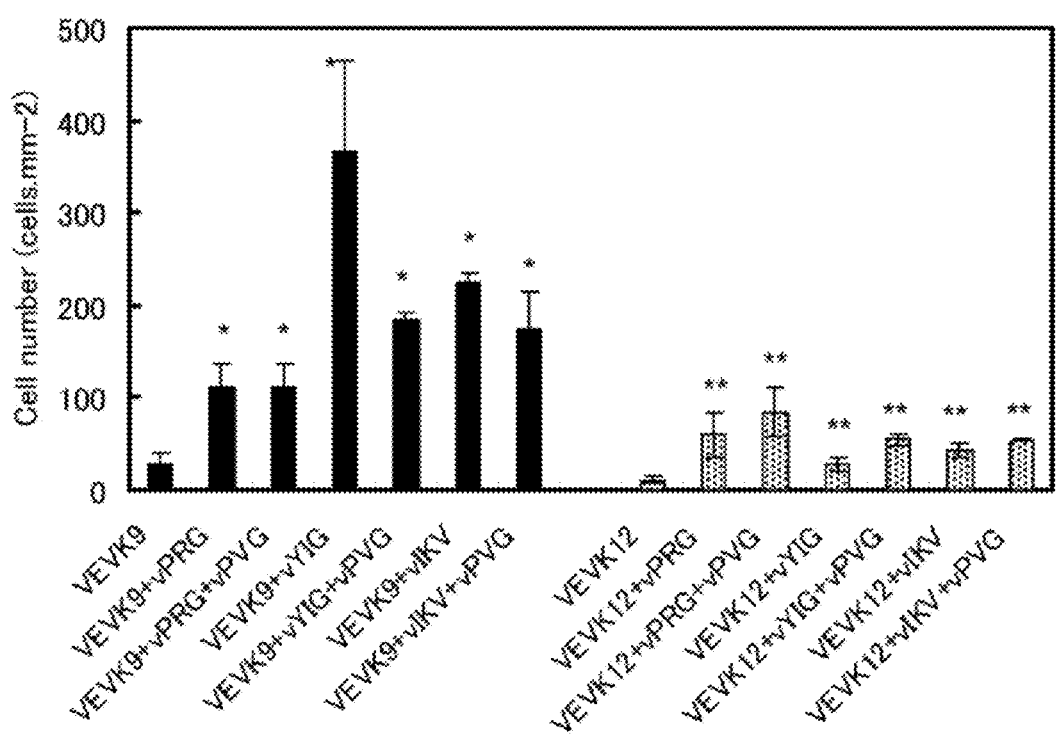
FIG. 9 is a bar graph showing cell numbers on each indicated functionalized peptide scaffold after three weeks cell culture. (A; VEVK9, B; vPRG_9, C; vPVG_vPRG_9, D; vYIG_9, E; vPVG_YIG_9, F; vIKV_9, G; vPVG_vIKV_9, H; VEVK12, I; vPRG_12, J; vPVG_vPRG_12, K; vYIG_12, L; vPVG_vYIG_9, M; vIKV_12, N; vPVG_vIKV_12).
Figure 10:
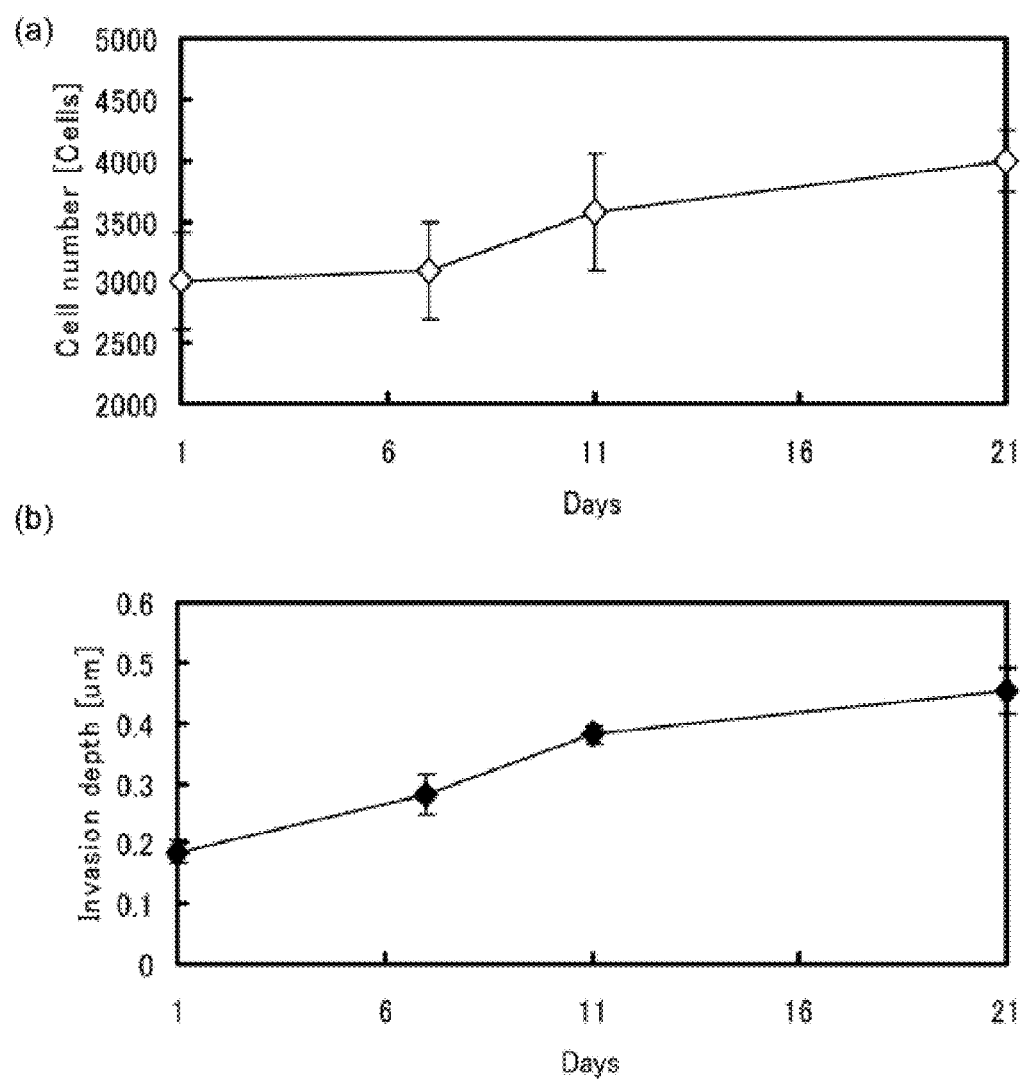
FIGS. 10A and 10B are line graphs showing cell growth in functionalized peptide scaffold vPVG_vPRG_9. (A) Cell number and (B) invasion depth were measured after 1 day, 7 days, 11 days and 21 days culture.

The peptide scaffolds vPVG_vPRG_9, vPVG_vPRG_12 showed significant cell migration into the scaffolds (FIG. 8).

These results suggest that MMP cleavage sites PVGLIG (SEQ ID NO: 19) of functionalized peptide sequence L were degraded by MMP periodontal ligament fibroblasts produced and then the fibroblasts could migrate into the scaffold easily.

Discussion

In Examples 1 to 3 above, we described the development of self-assembling peptide scaffolds with similar properties to natural extracellular matrix proteins for periodontal tissue regeneration. For example selected two sequence motifs from 2 unit RGD binding sequence PRGDSGYRGDS (SEQ ID NO: 15) and laminin cell adhesion motif PDSGR (SEQ ID NO:4). The two motifs seemed to be effective for periodontal ligament fibroblasts 3-D growth and collagens production from the fibroblast. The designer peptide scaffold PRG contains RGD cell attachment motif for integrin receptors. It has been reported that PRG promoted osteoblast activity for bone tissue regeneration and endothelial cell activity for angiogenesis [10a], [11a]. Another designer peptide scaffold PDS contains PDSGR (SEQ ID NO:4) cell attachment motif of laminin. It has been reported that periodontal ligament fibroblasts adhered to RGD motif, fibronectin and laminin, and expressed the integrin subunits related to the attachment to these extracellular matrix proteins [27a], [28a]. In this study, we showed that PRG and PDS promoted periodontal ligament fibroblasts activity. This suggests that periodontal ligament fibroblasts indeed recognized the exposed adhesion motifs attached to each scaffold through the integrin receptors for RGD motif or cell attachment motif of laminin PDSGR. Periodontal ligament fibroblasts adhered to the surface of these peptides recognized the adhesion motif inside of the scaffold as well and then migrated into these scaffolds.

It is known that growth factors and mechanical signals regulate the production of extracellular matrix proteins of fibroblasts [26a], [31a]-[38a]. Considering that no extra growth factors were added, our results suggest that the biochemical and perhaps mechanical signals from each different peptide scaffolds induced the production of extracellular matrix proteins. It has been previously reported that fibroblasts translate mechanical signals into changes in extracellular matrix production through the integrin [39a]-[41a]. They indicated that stretching of matrix-integrin contacts leads to cytoskeleton-mediated signals by rearrangement of cytoskeletal components that include actin filaments and recruitment of kinases such as focal adhesion kinase (FAK) and Src. Activation of FAK and Src further activate mitogen activated protein kinase (MAPK) signaling pathway to promote gene transcription. The altered gene transcription leads to translational and post-translational modification to selectively synthesize and secrete extracellular matrix proteins. In our study, it would appear that the interaction between integrin of the fibroblasts—cell adhesion motifs of the scaffolds PRG and PDS triggers an intracellular signaling pathway described above, then the fibroblasts synthesize and secrete type I and III collagens. On the other hand, since peptide scaffold RADA16 does not have cell adhesion motif, periodontal ligament fibroblasts seem to adhere to peptide by a different way. It has been assumed that interaction between charged residues of RADA16 and cell surface components play a role in non-integrin-mediated cell attachment to the peptide scaffold [42a], and cells adhere to the peptide scaffold via adhesion proteins which can be derived either from the serum of the added culture medium or produced by the cells [43a]. Periodontal ligament fibroblasts seem to adhere to the peptide scaffold RADA16 without the interaction between integrin-cell adhesion motifs of scaffold and not to produce collagens as in the case of the functionalized peptide scaffolds PRG and PDS. These results suggest that peptide scaffold functionalization with cell adhesion motifs which interact with integrin may be useful to stimulate matrix protein production from fibroblasts.

VEVK9 and VEVK12 are simple repeating units of amino acids VEVK (Valine-Glutamate-Valine-Lysine) which self-assemble into a nanofiber structure. The self-assembling peptide VEVK9 was functionalized either with RGD, laminin cell adhesion motifs or an MMP cleavable motif in order to mimic extracellular matrix to enhance cell maintenance and function in cell cultures. The functionalized peptides vPRG, vYIG and vIKV were synthesized with the VEVK9 sequence plus an additional motif added to the C-terminus using solid phase synthesis. One motif contains two repetitions of the RGD sequence (PRGDSGYRGDS (SEQ ID NO: 15)), and the others are cell adhesion motifs of laminin (YIGSR (SEQ ID NO: 5), IKVAV (SEQ ID NO: 6)). Glycine residues were used between the self-assembling motif VEVKVEVKV (SEQ ID NO: 2) and the functional motif as a spaced linker to keep the flexibility of the functional peptides. The MMP-2 cleavable motif (PVGLIG (SEQ ID NO: 11)) was inserted between two VEVK units. In comparison to RADA16-I and its functionalized peptides, these peptides are short sequences, maximum 20 amino acids (in vPRG), and seem to be cost-effective. The peptides were solubilized in water at a concentration of 10 mg/ml (1%, w/v). The peptides readily undergo self-assembly to form soft hydrogels. Mixing with self-assembling peptide VEVK9 or VEVK12 facilitated self-assembly and gelation. Tapping mode AFM was used to analyze the formation of nanofibers because this system allowed us to observe peptide filaments without damaging them. Self-assembling peptides VEVK12 and VEVK9 mixed with functionalized peptides vPRG and vPVG formed nanofibers in aqueous solutions.

In order to evaluate cell attachment on each peptide scaffold, the same number of cells were seeded on each scaffold and cultured for three weeks. The fibroblasts exhibited good attachment and extension on the peptide scaffolds functionalized with vPRG, vYIG and vIKV, particularly on VEVK9 mixed with vYIG and vIKV. In contrast, on non-functionalized peptide scaffolds VEVK9 and VEVK12 cells are sparse and have a rounded morphology. All functionalized peptides tested here significantly promoted cell proliferation, especially in scaffolds made with VEVK9.

It is known that periodontal ligament fibroblasts adhere to the RGD motif, fibronectin and laminin and express the integrin subunits related to the attachment to these extracellular matrix proteins [28b, 29b]. Thus, the inclusion of these cell adhesion motifs in the peptide scaffolds seems to promote the fibroblasts' adhesion, proliferation and 3-D migration through the interaction with integrin receptors of the fibroblasts. Interestingly, these results showed the differences in effectiveness of the functionalized motifs between the self-assembling peptides VEVK9 and VEVK12. Functionalized peptide motifs included in the peptide scaffold VEVK9 are more effective for cell proliferation than those in VEVK12. It has been reported that a functional motif physically incorporated into the nanofibers of a scaffold affects cell growth[8b]. It appeared in this study that the functionalized peptides are incorporated well in self-assembling peptide VEVK9 to form nanofibers with the functional motifs.

We previously showed that cells spontaneously migrate into the 3D scaffold using 3-D image collections and reconstructions obtained by confocal microscopy [8b]. The reconstructed images of periodontal ligament fibroblasts in the peptide scaffold VEVK9, VEVK9 mixed with functionalized peptide vPRG alone, mixed with vPRG and vPVG, mixed with vYIG and vPVG, and mixed with vIKV and vPVG. Migrating cells were clearly discernible by confocal imaging and differences in the characteristics of these scaffolds were found. Only a few fibroblasts adhered to the peptide scaffold with VEVK9, and these remained near the surface. In peptide scaffolds with VEVK9 mixed with functionalized peptides, a large number of cells appeared on surface and inside of the scaffolds. Furthermore, we showed that the fibroblasts initially attached to the surface of the scaffold at day 1 proliferated as well as migrated into the scaffold spontaneously. The images exhibit significant increases in fibroblast proliferation and migration due to the effects of the functionalized peptides vPRG and vPVG. It appears that the fibroblasts on the surface of the scaffold migrated into the scaffold to enlarge their sphere of activity.

It is known that periodontal ligament fibroblasts contribute greatly to the remodeling of periodontal tissue by secreting MMP-2 for degradation and synthesizing extracellular matrix proteins for replacement [30b]. It is also known that MMP regulation occurs by integrin binding, for example by $\alpha_v\beta_3$, which is the main RGD-binding integrin [31b]. They suggest that the fibroblasts recognized the exposed RGD adhesion motifs of the scaffold via integrin receptors to adhere to the scaffold. The interaction between the integrin and the RGD motifs yields MMP-2 production by the fibroblasts. As a result, the fibroblasts moved deeper into the scaffold, breaking the MMP cleavable sites incorporated into the scaffold. Interestingly, in the case of VEVK9 mixed with only vPVG (without vPRG), the fibroblasts were rounded on surface of the scaffold and did not proliferate or migrate into the scaffold, which is similar to the case of VEVK9. Thus, a cell adhesion motif which interacts with integrin seems to play an important role as a stimulus for proteolytic cell migration into the enzymatically degradable scaffold [21b]. In the case of scaffolds functionalized with laminin cell adhesion motifs vYIG and vIKV, the fibroblasts appear to migrate into them in the same manner.

A variety of functionalized peptide scaffolds have been developed and shown a great potential for tissue engineering and regenerative medicine [7b, 8b, 25b]. Most of them are functionalized with cell adhesion motifs derived from extracellular matrix proteins. They are responsible for the first interaction between cell and matrix, cell adhesion to promote cell growth included cell migration. But since these functionalized peptide scaffolds are not enzymatically degradable, their ability to promote cell migration is limited. In the nondegradable scaffolds, cells seem to squeeze through the spaces between nanofibers of the scaffolds. As an ameboid cell migration depends on the mechanical properties of the peptide scaffold, the strategy of using a cell adhesion motif is limited to scaffolds with relatively large pores and soft nanofibers which cells can penetrate. In contrast, enzymatically degradable peptide scaffolds enable a significant increase in cell migration. The peptide scaffolds functionalized with vPVG seem to be enzymatically degradable and promoted proteolytic cell migration. The MMP cleavable motif tested here may be useful to functionalize most of self-assembling peptides without considering the mechanical properties. Also, when combined with a cell adhesion motif in varying proportions, it would be possible to design suitable peptide scaffolds for specific applications. For example, these peptide scaffolds may be useful as alternatives for naturally occurring extracellular matrix derived materials such as fibrin or collagen, which require difficult purification procedures and carry the risks of immunogenicity and disease transmission.

We here demonstrated that fully designer peptide scaffolds significantly accelerated periodontal ligament proliferation and migration. This is a significant finding that these simple motifs could have a drastic influence on the fibroblasts'activities. It is much easier and less expensive to produce the peptide scaffold than to use complex and expensive soluble factors that show similar cell behavior. These peptide scaffolds have potential value as scaffold materials for tissue engineering and regenerative medicine, for example periodontal tissue reconstruction.

The periodontium, the supporting teeth apparatus, consists of four tissues, gingival, periodontal ligament, cementum and alveolar bone. The diverse composition of the periodontium makes periodontal wound healing a complex process because of the interaction between hard and soft connective tissues, implying the selective repopulation of the root surface by cells capable of reforming the cellular and extracellular components of new periodontal ligament, cementum and alveolar bone [44a]. Guided tissue regeneration is a conventional method for periodontal tissue reconstruction, which could be driven by excluding or restricting the repopulation of periodontal defects by epithelial and gingival connective cells, providing space and favorable niche to maximize periodontal ligament fibroblasts, cementoblasts and osteoblasts to migrate selectively, proliferate and differentiate. Considering the clinical use of these scaffolds for periodontal tissue reconstruction, they are required to provide the selective cell repopulations. It has been previously reported that the peptide scaffolds PRG could control osteoblasts activities by changing the concentration of the designer peptide containing two unit of RGD [10a]. It also has been reported that laminin has specific cell adhesion properties, which periodontal ligament fibroblasts and osteoblasts could adhere well, compared with gingival fibroblasts [27a]-[29a]. They suggest that these peptide scaffolds PRG and PDS with laminin cell adhesion motif might be useful as periodontal tissue filler with selective cell repopulation properties.

For successful clinical use of in periodontal tissue reconstruction, functionalized peptide scaffolds would be required to allow selective cell repopulations and promote angiogenesis. It has been previously reported that the peptide scaffold functionalized with RGD could control osteoblasts' activities by changing the concentration of the functionalized peptide[8]. It also has been reported that laminin has specific cell adhesion properties, which favored adhesion by periodontal ligament fibroblasts and osteoblasts over adhesion by gingival fibroblasts [28b, 29b]. For angiogenesis, the above-mentioned peptide scaffold functionalized with RGD was also shown to promote endothelial cell growth [25b]. Furthermore the functionalized peptide vPVG tested here seems to be effective for endothelial cell proteolytic migration. A variety of functionalizations of the self-assembling peptides will enable optimization of the scaffolding materials for many uses, included periodontal tissue reconstruction.

In the above-described studies, designer functionalized peptide scaffolds PRG and PDS have been demonstrated to significantly enhance periodontal ligament fibroblasts proliferation, migration and extracellular matrix protein type I and type III collagen production in cell culture. Furthermore, we have developed and evaluated self-assembling peptides VEVK9, VEVK12 and functionalized designer self-assembling peptide scaffolds with cell adhesion motifs and MMP cleavage sites. These functionalized peptide scaffolds have been shown to significantly enhance periodontal ligament fibroblast proliferation and migration in 3D cell culture independent of scaffold stiffness. Thus the designer scaffolds described herein will be widely useful in tissue engineering and regenerative medicine.

References

1a Zhang S (2003) Fabrication of novel biomaterials through molecular self-assembly. Nat Biotechnology 21: 1171-1178.
2a Zhang S, Holmes T, Lockshin C, Rich A (1993) Spontaneous assembly of a self-complementary oligopeptide to form a stable macroscopic membrane. Proc Natl Acad Sci USA 90: 3334-3338.
3a Zhang S, Holmes T C, DiPersio C M, Hynes R O, Su X, et al. (1995) Self-complementary oligopeptide matrices support mammalian cell attachment. Biomaterials 16: 1385-1393.
4a Koutsopoulos S, Unsworth L D, Nagai Y, Zhang S (2009) Controlled release of functional proteins through designer self-assembling peptide nanofiber hydrogel scaffold. Proc Natl Acad Sci USA 106: 4623-4628.
5a Yang Y, Khoe U, Wang X, Horii A, Yokoi H, et al. (2009) Designer self-assembling peptide nanomaterials. Nano Today 4: 193-210.
6a Yokoi H, Kinoshita T, Zhang S (2005) Dynamic reassembly of peptide RADA16 nanofiber scaffold. Proc Natl Acad Sci USA 102: 8414-8419.
7a Zhang S, Spirio L, Zhao X (2005) PuraMatrix: Self-assembling peptide Nanofiber Scaffolds. Scaffolding in Tissue Engineering. Boca Raton, Fla. USA: Taylor & Francis. pp. 218-238.
8a Ellis-Behnke R G, Liang Y X, You S W, Tay D, Zhang S (2006) Nano neuro knitting: Peptide nanofiber scaffold for brain repair and axon regeneration with functional return of vision. Proc Natl Acad Sci USA 103: 5054-5059.
9a Gelain F, Bottai D, Vescovi A, Zhang S (2006) Designer self-assembling peptide nanofiber scaffolds for adult mouse neural stem cell 3-dimensional culture. PloS ONE 1: e1191-11.
10a Horii A, Wang X M, Gelain F, Zhang S (2007) Biological designer self-assembling peptide nanofiber scaffolds significantly enhance osteoblast proliferation, differentiation and 3-D migration. PloS ONE 2: e190.
11a Wang X, Horii A, Zhang S (2008) Designer functionalized self-assembling peptide nanofiber scaffolds for growth, migration, and tubulogenesis of human umbilical vein endothelial cells. Soft Matter 4: 2388-2395.
12a Nyman S, Lindhe J, Karring T, Rylander H (1982) New attachment following surgical treatment of human periodontal disease. J Clin Periodontol 9: 290-296.
13a Lindhe J, Pontoriero R, Verglundh T, Araujo M (1995) The effect of flap management and bioresorbable occlusive devices in GTR treatment of degree III furcation defects. An experimental study in dogs. J Clin Periodontol 22: 276-83.
14a Park J B, Matsuura M, Han K Y, Norderyd O, Lin W L, et al. (1995) Periodontal regeneration in class IIIfurcation defects of beagle dogs using guided tissue regenerative therapy with platelet-derived growth factor. J Periodontol 66: 462-77.
15a Gantes B, Martin M, Garrett S, Egelgerg J (1988) Treatment of periodontal defects. (II). Bone regeneration in mandibular class II defects. J Clin Periodontol 15: 232-239.
16a Camelo M, Nevins M L, Schenk R K, Simion M, Rasperini G, et al. (1998) Clinical, radiographic and histologic evaluation of human periodontal defects treated with Bio-Oss and Bio-Gide. Int J Periodontics Restorative Dent 18: 321-31.
17a Hammastorom L (1997) Enamel matrix, cementum development and regeneration. J Clin Periodontol 24: 658-668.
18a Hammarstrom L, Heijl L, Gestrelius S (1997) Periodontal regeneration in a buccal dehiscence model in monkeys after application of enamel matrix proteins. J Clin Periodontol 24: 669-677.
19a Windisch P, Sculean A, Klein F, Toth V, Gera I, et al. (2002) Comparison of clinical radiographic, hisometric measurements following treatment with guided tissue regeneration or enamel matrix proteins in human periodontal defects. J Periodontol 73: 409-417.
20a Giannoble W V (1996) Periodontal tissue engineering by growth factors. Bone 19: 23S-37S.
21a Nevins M, Giannobile W V, McGuire M K, Kao R T, Mellonig J T, et al. (2005) Platelet-derived growth factor stimulates bone fill and rate of attachment level gain: Results of a large multicenter randomized controlled trial. J Periodontol 76: 2205-2215.
22a Murakami S, Takayama S, Kitamura M, Shimabukuro M, Yanagi Y, et al. (2003) Recombinat human basic fibroblasts growth factor (bFGF) stimulates periodontal regeneration in class II furcation defects created in beagle dogs. J Periodont Res 38: 97-103.
23a Takeda K, Shiba H, Mizuno N, Hasegawa N, Mouri Y (2005) Brain-derived neurotrophic factor enhances periodontal tissue regeneration. Tissue Engineering 11: 1618-1629.
24a Jovanovic S A, Hunt D R, Bernard G W, Spiekermann H, Wozney J M, et al. (2006) Bone reconstruction following implantation of rh BMP-2 and guided bone regeneration in canine alveolar ridge defects. Clin Oral Impl Res 18: 224-230.
25a Okubo K, Kobayashi M, Takiguchi T, Takada T, Ohazama A, et al. (2003) Participation of endogenus IGF-I and TGF-beta1 with enamel matrix derivative-stimulated cell growth in human periodontal ligament cells. J Periodont Res 38: 1-9.
26a Matsuda N, Lin W L, Kumar N M, Cho M I, Genco R J (1992) Mitogenic, chemotactic, and synthetic responses of rat periodontal ligament fibroblastic cells to polypeptide growth factors in vitro. J Periodontol 63: 515-525.
27a Palaiologou A A, Yukna R A, Moses R, Lallier T E (2001) Gingival, dermal, and periodontal ligament fibroblastss express different extracellular matrix receptors. J Periodontol 72: 798-807.
28a Giannopoulou C, Cimasoni G (1996) Functional characteristics of gingival and periodontal ligament fibroblastss. J Dent Res 75: 895-902.
29a Grzesik W J, Ivanov B, Robey F A, Southerland J, Yamauchi M (1998) Synthetic integrin-binding peptides promote adhesion and proliferation of huma periodontal ligament cells in vitro. J Dent Res 77: 1606-1612.
30a Berkovits B K B (1990) The structure of the periodontal ligament: an update. European J Orthodontics 12: 51-76.
31a Takayama S, Murakami S, Miki Y, Ikezawa K, Tasaka S (1997) Effects of basic fibroblasts growth factor on human periodontal ligament cells. J Periodont Res 32: 667-675.

32a MacKenna D, Summerour S R, Villarreal F J (2000) Role of mechanical factors in modulating cardiac fibroblast function and extracellular matrix synthesis. Cardiovasc Res 46: 257-263.

33a Chiquet M, Tunc-Civelek V, Sarasa-Renedo A (2007) Gene regulation by mechanotransduction in fibroblasts. Appl Physiol Nutr Metab 32: 967-973.

34a Chiquet M, Renedo A S, Huber F, Fluck M (2003) How do fibroblasts translate mechanical signals into changes in extracellular matrix production? Matrix Biology 22: 73-80.

35a Karimbux N Y, Nishimura I (1995) Temporal and spatial expressions of type XII collagen into remodeling periodontal ligament during experimental tooth movement. J Dent Res 73: 313-318.

36a Centrella M, McCarthy T L, Canalis E (1987) Transforming growth factor beta is a bifunctional regulator replication and collagen synthesis in osteoblast-enriched cell cultures from fetal rat bone. J Biol Chem 262: 2869-2874.

37a Keshi-Oja J, Raghow R, Sadwy M, Loskutoff D J, Postlethwaite A E, et al. (1988) Regulation of the mRNAs for type I plasminogen activator inhibitor, fibronectin, and type I procollagen by transforming growth factor-$\beta$. Divergent responses in lung fibroblasts and carcinoma cells. J Biol Chem 263: 3111-3115.

38a Wrana J L, Macho M, Hawrylyshyn B, Yao K L, Domenicussi C, et al. (1988) Differential effects of transforming growth factor-$\beta$ on the synthesis of extracellular matrix proteins by normal fetal rat calvarial bone cell population. J Cell Biol 106: 915-924.

39a Choquet D, Felsenfeld D P, Sheetz M P (1997) Extracellular matrix rigidity causes strengthening of integrin-cytoskeleton linkages. Cell 88: 39-48.

40a Gelbraith C G, Sheetz M P (1998) Forces on adhesive contracts affect cell function. Curr Opin Cell Biol 10: 566-571.

41a Shyy J Y-J, Chien S (1997) Role of integrins in cellular responses to mechanical stress and adhesion. Curr Opin Cell Biol 9: 707-713.

42a Zhang S, Holmes T C, DiPersio C M, Hynes R O, Su X, et al. (1995) Self-complementary oligopeptide matrices support mammalian cell attachment. Biomaterial 16: 1385-1393.

43a Sieminski A L, Semino C E, Gong H, Kamm R D (2008) Primary sequence of ionic self-assembling peptide gels affects endothelial cell adhesion and capillary morphogenesis. J Biomed Mater Res A 87: 494-504.

44a Taba M Jr, Jin Q, Sugai J V, Giannobile W V (2005) Current concepts in periodontal bioengineering. Orthod Craniofacial Res 8: 292-302.

1b S. Zhang, T. C. Holmes, C. Lockshin, A. Rich, *Proc Natl Aead Sci USA,* 1993, 90, 3334-3338.

2b S. Zhang, T. C. Holmes, C. M. DiPersio, R. O. Hynes, X. Su, A. Rich, *Biomaterials,* 1995, 16, 1385-1393.

3b S. Koutsopoulos, L. D. Unsworth, Y. Nagai, S. Zhang, *Proc Natl Acad Sci USA,* 2009, 106, 4623-4628.

4b Y. Yang, U. Khoe, X. Wang, A. Horii, H. Yokoi, S. Zhang, *Nano Today,* 2009, 4, 193-210

5b H. Yokoi, T. Kinoshita, S. Zhang, *Proc Natl Acad Sci USA,* 2005, 102, 8414-8419.

6b R. G. Ellis-Behnke, Y. X. Liang, S. W. You, D. Tay, S. Zhang, *Proc Natl Acad Sci USA,* 2006, 103: 5054-5059.

7b R. G. Ellis-Behnke, Y. X. Liang, D. Tay, P. W. F. Kau, G. E. Schneider, S. Zhang, W. Wu, K. F. So, *Nanomedicine: Nanotechnology, Biology & Medicine* 2006, 2, 207-215.

8b A. Horii, X. M. Wang, F. Gelain, S. Zhang, *PLoS ONE,* 2007, 2, e190.

9b F. Gelain, D. Bottai, A. Vescovi, S. Zhang, *PLoS ONE,* 2006, 1, e1191-11.

10b J. Kisiday, M. Jin, B. Kurz, H. Hung, C. E. Semino, S. Zhang, A. J. Grodzinsky, *Proc Natl Acad Sci USA,* 2002, 99, 9996-10001.

11b E. J. Leon, N. Verma, S. Zhang, D. A. Lauffenburger, R. D. Kamm, *J Biomaterials Science,* 1998, 9, 297-312.

12b M. Caplan, P. Moore, S. Zhang, R. D. Kamm, D. A. Lauffenburger, *Biomacromolecules,* 2000, 1, 627-631.

13b M. Caplan, E. M. Schwartzharb, S. Zhang, R. D. Kamm, D. A. Lauffenburger, *Biomaterials,* 2002, 23, 219-227.

14b M. Caplan, E. M. Schwartzfarb, S. Zhang, R. D. Kamm, D. A. Lauffenburger, *J Biomaterials Science Polymer Edition,* 2002, 13, 225-236.

15b D. Marini, W. M. Hwang, D. A. Lauffenburger, S. Zhang, R. D. Kamm, *Nano Letters,* 2002, 2, 295-299.

16b W. M. Hwang, D. Marini, R. D. Kamm, S. Zhang, *J Chem Physics,* 2003, 118, 389-397.

17b M. P. Lutolf, J. L. Lauer-Fields, H. G. Schmoekel, A. T. Metters, F. E. Weber, G. B. Fields. *Proc Natl Acad Sci USA,* 2003, 100, 5413-5418.

18b H. W. Jun, V. Yuwono, S. E. Paramonov, J. D. Hartgerink, *Adv Mater,* 2005, 17, 2612-2617.

19b Y. Chau, Y. Luo, A. C. Y. Cheung, Y. Nagai, S. Zhang, J. B. Kobler, S. M. Zeitels and R. S. Langer, *Biomaterials,* 2008, 29, 1713-1719.

20b B. Law, R. Weissleder and C. H. Tung, *Biomacromolecules,* 2006, 7, 1261-1265.

21b M. P. Lutolf, F. E. Weber, H. G. Schmoekel, J. C. Schense, T. Kohler, R Muller and J. A. Hubbell, *Nature Biotechnology,* 2003, 21, 513-518.

22b D. Seliktar, A. H. Zisch, M. P. Lutolf, J. L. Wrana and J. A. Hubbell, *J of Biomedical Materials Research part A,* 2004, 68, 704-716.

23b C. B. Bahney, C. W. Hsu, J. West and B. Johnstone, presented in part at Society for Biomaterials 2009 Annual meeting and exposition, San Antonio, April, 2009.

24b C. A. DeForest, E. A. Sims, B. D. Polizzotti and K. S. Anseth, presented in part at Society for Biomaterials 2009 Annual meeting and exposition, San Antonio, April, 2009.

25b X. M. Wang, A. Horii, S. Zhang, *Soft Matter,* 2008, 4, 2388-2395.

26b B. E. Turk, L. L. Huang, E. T. Piro and L. C. Cantley, *Nature Biotechnology,* 2001, 19, 661-667.

27b J. L. Hutter and J. Bechhoefer, *Rev. Sci. Instrum,* 1993, 64, 1868-1873.

28b A. A. Palaiologou, R. A. Yukna, R. Moses, T. E. Lallier, *J Periodontol,* 2001, 72, 798-807.

29b C. Giannopoulou, G. Cimasoni, *J Dent Res,* 1996, 75, 895-902.

30b E. Tsuruga, K. Irie and T. Yajima, *J Dent Res,* 2007, 86(4), 352-356.

31b Xu J, Rodrigues D, Petitelerc E, Kim J J, Hangai M, Yuen S M, Davis G E, Brooks P C, *J Cell Biol,* 2001, 154, 1069-1079.

32b M. Taba Jr, Q. Jin, J. V. Sugai, W. V. Giannobile, *Orthod Craniofacial Res,* 2005, 8, 292-302.

33b S. Nyman, J. Lindhe, T. Karring, H. Rylander, *J Clin Periodontol,* 1982, 9, 290-296.

34b J. Lindhe, R. Pontoriero, T. Verglundh, M. Araujo, *J Clin Periodontol,* 1995, 22, 276-83.

35b J. B. Park, M. Matsuura, K. Y. Han, O. Norderyd, W. L. Lin, R. I. Genco, M. I. Cho, *J Periodontol,* 1995, 66, 462-77.

36b M. S. McKay, E. Olson, M. A. Hesla, A. Panyutich, T. Ganz, S. Perkins, *Oral Microbiol Immunol,* 1999, 14, 190-193.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for regenerating a dental tissue in a patient in need thereof comprising administering to the dental tissue of said patient an effective amount of a self-assembling peptide, wherein the self-assembling peptide comprises:
   a. a first amino acid domain that mediates self-assembly, wherein the domain comprises alternating hydrophobic and hydrophilic amino acids that are complementary and structurally compatible and wherein said domain self-assembles into a macroscopic structure when present in unmodified form, wherein the first amino acid domain has the sequence VEVKVEVKV (SEQ ID NO: 2) or VEVKVEVKVEVK (SEQ ID NO: 3); and
   b. a second amino acid domain that does not mediate self-assembly in isolated form, wherein the second amino acid domain comprises a biologically active motif.

2. The method of claim 1, wherein the dental tissue is periodontal ligament tissue.

3. The method of claim 1, wherein the biologically active motif is a laminin cell adhesion motif.

4. The method of claim 1, wherein the second amino acid domain comprises a sequence selected from the group consisting of PDGSR (SEQ ID NO: 4), YIGSR (SEQ ID NO: 5), IKVAV (SEQ ID NO: 6), LRE (SEQ ID NO: 7), RNIAEIIKDI (SEQ ID NO:8), RYVVLPR (SEQ ID NO: 9), LGTIPG (SEQ ID NO: 10), PVGLIG (SEQ ID NO: 19) and GPVGLIG (SEQ ID NO: 12).

5. The method of claim 1, wherein the second amino acid domain comprises an RGD peptide.

6. The method of claim 1, wherein the second amino acid domain comprises a matrix metalloproteinase cleavable substrate.

7. The method of claim 6, wherein the second amino acid domain comprises the sequence PVGLIG (SEQ ID NO: 19).

8. A method of treating periodontal disease in a patient in need thereof comprising administering to the periodontium of said patient an effective amount of a self-assembling peptide, wherein the self-assembling peptide comprises:
   a. a first amino acid domain that mediates self-assembly, wherein the domain comprises alternating hydrophobic and hydrophilic amino acids that are complementary and structurally compatible and wherein said domain self-assembles into a macroscopic structure when present in unmodified form, wherein the first amino acid domain has the sequence VEVKVEVKV (SEQ ID NO: 2) or VEVKVEVKVEVK (SEQ ID NO: 3); and
   b. a second amino acid domain that does not mediate self-assembly in isolated form, wherein the second amino acid domain comprises a biologically active motif.

9. The method of claim 8, wherein the method further comprises administering an effective amount of a solid biomaterial.

10. The method of claim 9, wherein the biomaterial comprises calcium, phosphorous or a combination thereof.

11. The method of claim 9, wherein the biomaterial comprises pores having a diameter from about 100 to about 500 microns.

* * * * *